(12) United States Patent
Myrick

(10) Patent No.: US 6,529,276 B1
(45) Date of Patent: Mar. 4, 2003

(54) OPTICAL COMPUTATIONAL SYSTEM

(75) Inventor: Michael L. Myrick, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 09/286,881

(22) Filed: Apr. 6, 1999

(51) Int. Cl.[7] .............................. G01N 21/25; G06E 1/00
(52) U.S. Cl. ...................... 356/419; 356/310; 356/330; 706/40
(58) Field of Search ............................... 356/402, 409, 356/416, 419, 310, 330; 706/40

(56) References Cited

U.S. PATENT DOCUMENTS

| | | | |
|---|---|---|---|
| 4,084,880 A | 4/1978 | Clow .......................... 350/3.72 |
| 4,118,106 A | 10/1978 | Leith .......................... 350/96.25 |
| 4,687,335 A | 8/1987 | Zupanick et al. ............ 356/416 |
| 4,821,338 A | 4/1989 | Naruse et al. ............... 455/617 |
| 4,934,782 A | 6/1990 | Soffer et al. ............. 350/162.12 |
| 5,005,946 A | 4/1991 | Brandstetter ............ 350/162.12 |
| 5,029,245 A | 7/1991 | Keranen et al. ............ 250/205 |
| 5,090,807 A | 2/1992 | Tai ............................... 356/310 |
| 5,194,921 A | 3/1993 | Tambo et al. ............... 356/432 |
| 5,289,289 A | 2/1994 | Nagasaki ..................... 358/432 |
| 5,321,539 A | 6/1994 | Hirabayashi et al. ......... 359/94 |
| 5,412,465 A | 5/1995 | Baylor et al. ................ 356/301 |
| 5,424,545 A * | 6/1995 | Block et al. ................. 356/405 |
| 5,459,677 A | 10/1995 | Kowalski et al. ......... 364/571.02 |
| 5,479,164 A | 12/1995 | Yorks et al. .................. 341/50 |
| 5,513,022 A | 4/1996 | Son et al. ...................... 359/16 |
| 5,555,128 A | 9/1996 | Khoury et al. ............... 359/559 |
| 5,717,605 A * | 2/1998 | Komiya et al. ............... 356/402 |
| 5,737,076 A | 4/1998 | Glaus et al. .................. 356/310 |
| 5,747,806 A | 5/1998 | Khalil et al. ............ 250/339.12 |
| 5,750,994 A | 5/1998 | Schlager ................. 250/339.11 |
| 5,771,096 A | 6/1998 | Andersen ..................... 356/346 |
| 5,828,492 A | 10/1998 | Moser et al. ................. 359/575 |
| 5,945,676 A | 8/1999 | Khalil et al. ............ 250/339.12 |
| 6,040,578 A * | 3/2000 | Malin et al. ............ 250/339.12 |
| 6,198,531 B1 | 3/2001 | Myrick et al. ............... 356/300 |
| 6,236,047 B1 | 5/2001 | Malin et al. ............ 250/339.12 |

FOREIGN PATENT DOCUMENTS

| | | |
|---|---|---|
| EP | 0600334 A2 | 6/1994 |
| JP | 04001558 | 7/1992 |
| JP | 11506206 | 2/1999 |
| JP | 11506207 | 2/1999 |
| WO | WO 9630746 | 10/1996 |

OTHER PUBLICATIONS

Photographs of Buhler System.

J.A. Dobrowolski and R.A. Kemp, "Refinement of Optical Multilayer Systems With Different Optimization Procedures," *Applied Optics*, vol. 29; No. 19, Jul. 1990, pp. 2876–2893.

Brian T. Sullivan and J.A. Dobrowolski, "Implementation of Numerical Needle Method for Thin–Film Design," *Applied Optics*, vol. 35; No. 28, Oct. 1996, pp. 5484–5492.

(List continued on next page.)

*Primary Examiner*—Frank G. Font
*Assistant Examiner*—Roy M. Punnoose
(74) *Attorney, Agent, or Firm*—Nelson Mullins Riley & Scarborough, LLP

(57) ABSTRACT

In optical filter systems and optical transmission systems, an optical filter compresses data into and/or derives data from a light signal. The filter way weight an incident light signal by wavelength over a predetermined wavelength range according to a predetermined function so that the filter performs the dot product of the light signal and the function.

5 Claims, 20 Drawing Sheets

OTHER PUBLICATIONS

A.G. Ryabenko and G.G. Kasparov, "An Algorithm for Constructing the Basis of Optimal Linear Combinations. Spectral Determination of Aerosol Impurities against the Background of a Water Aerosol with an Arbitrary Particle Size Distribution," *Pattern Recognition and Image Analysis*, vol. 3; No. 1, Mar. 1993, pp. 348–354.

A.G. Ryabenko and G.G Kasparov, "Numerical Study of a Pattern Recognition Multispectral System with Optimal Spectral Splitting," *Pattern Recognition and Image Analysis*, vol. 1; No. 3, 1991, pp. 57–68.

Vasil'ev, et al, "Rotational and Vibrational Deactivation of Excited HF Molecules," *Sov. Physics—JETP*, vol. 41; No. 4, 1976, pp. 617–621.

Moravskii, et al., "Spectrophotometric Determination of the Yield of the $C_{60}$ and $C_{70}$ Fullerenes in Electric Arc Synthesis under Helium," *Journal of Analytical Chemistry*, vol. 53; No. 12, 1998, pp. 1135–1142.

* cited by examiner

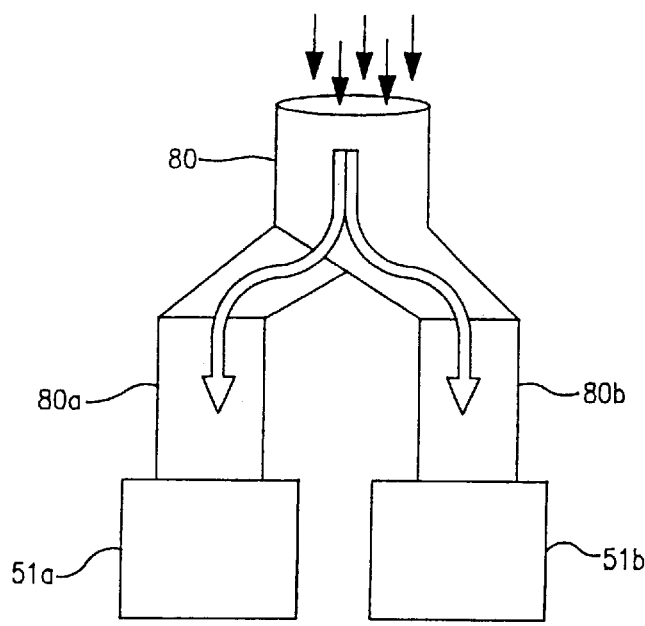
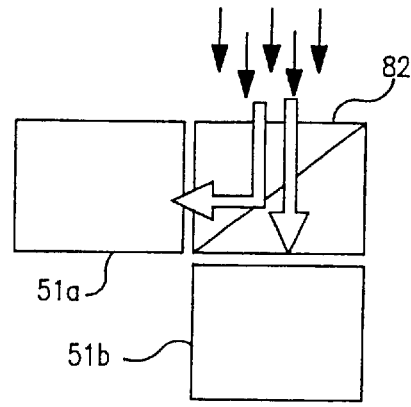
FIG. 8A
FIG. 8B
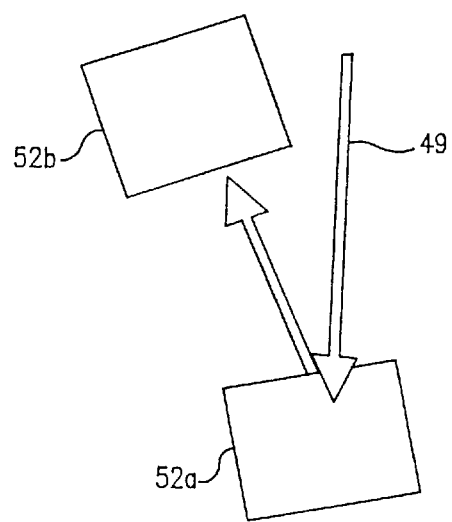
FIG. 8C

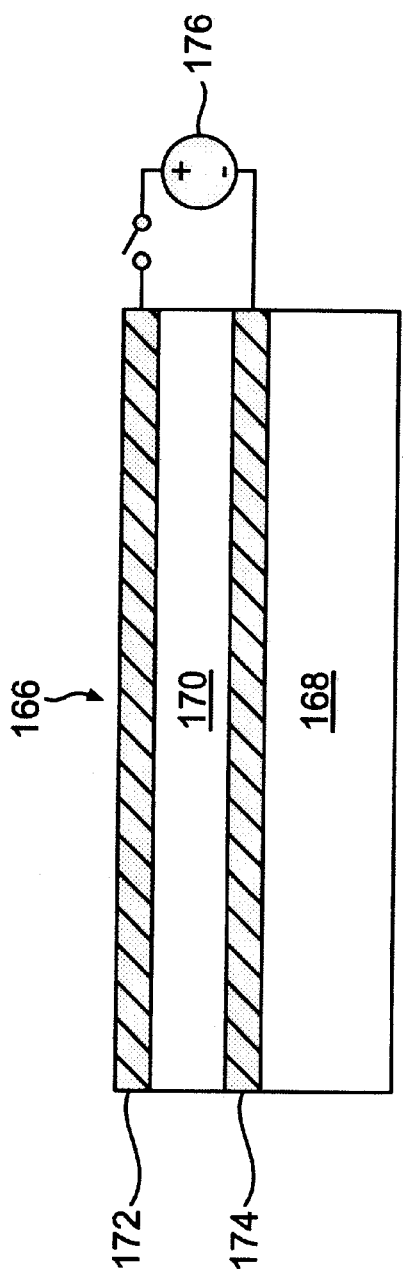
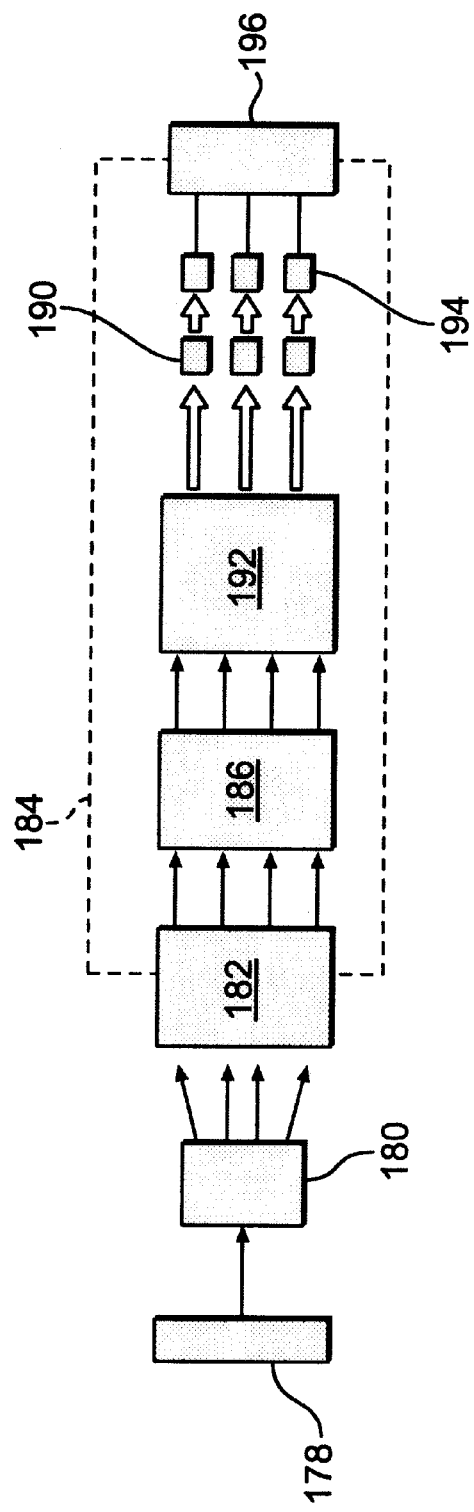
FIG. 14
FIG. 15

OPTICAL COMPUTATIONAL SYSTEM

BACKGROUND OF THE INVENTION

The present invention relates to spectroscopy analysis systems. More particularly, the invention relates to improvements in the compression of data carried by light so that information about the light may be obtained.

Light conveys information through data. When light interacts with matter, for example, it carries away information about the physical and chemical properties of the matter. A property of the light, for example its intensity, may be measured and interpreted to provide information about the matter with which it interacted. That is, the data carried by the light through its intensity may be measured to derive information about the matter. Similarly, in optical communications systems, light data is manipulated to convey information over an optical transmission medium, for example fiber optic cable. The data is measured when the light signal is received to derive information.

In general, a simple measurement of light intensity is difficult to convert to information because it likely contains interfering data. That is, several factors may contribute to the intensity of light, even in a relatively restricted wavelength range. It is often impossible to adequately measure the data relating to one of these factors since the contribution of the other factors is unknown.

It is possible, however, to derive information from light. An estimate may be obtained, for example, by separating light from several samples into wavelength bands and performing a multiple linear regression of the intensity of these bands against the results of conventional measurements of the desired information for each sample. For example, a polymer sample may be illuminated so that light from the polymer carries information such as the sample's ethylene content. Light from each of several samples may be directed to a series of bandpass filters which separate predetermined wavelength bands from the light. Light detectors following the bandpass filters measure the intensity of each light band. If the ethylene content of each polymer sample is measured using conventional means, a multiple linear regression of ten measured bandpass intensities against the measured ethylene content for each sample may produce an equation such as:

$$y = a_0 + a_1 w_1 + a_2 w_2 + \ldots + a_{10} w_{10} \quad \text{(Equation 1)},$$

where y is ethylene content, $a_n$ are constants determined by the regression analysis, and $w_n$ is light intensity for each wavelength band.

Equation 1 may be used to estimate ethylene content of subsequent samples of the same polymer type. Depending on the circumstances, however, the estimate may be unacceptably inaccurate since factors other than ethylene may affect the intensity of the wavelength bands. These other factors may not change from one sample to the next in a manner consistent with ethylene.

A more accurate estimate may be obtained by compressing the data carried by the light into principal components. To obtain the principal components, spectroscopic data is collected for a variety of samples of the same type of light, for example from illuminated samples of the same type of polymer. For example, the light samples may be spread into their wavelength spectra by a spectrograph so that the magnitude of each light sample at each wavelength may be measured. This data is then pooled and subjected to a linear-algebraic process known as singular value decomposition (SVD). SVD is at the heart of principal component analysis, which should be well understood in this art. Briefly, principal component analysis is a dimension reduction technique which takes m spectra with n independent variables and constructs a new set of eigenvectors that are linear combinations of the original variables. The eigenvectors may be considered a new set of plotting axes. The primary axis, termed the first principal component, is the vector which describes most of the data variability. Subsequent principal components describe successively less sample variability, until only noise is described by the higher order principal components.

Typically, the principal components are determined as normalized vectors. Thus, each component of a light sample may be expressed as $x_n z_n$, where $x_n$ is a scalar multiplier and $z_n$ is the normalized component vector for the $n^{th}$ component. That is, $z_n$ is a vector in a multi-dimensional space where each wavelength is a dimension. As should be well understood, normalization determines values for a component at each wavelength so that the component maintains it shape and so that the length of the principal component vector is equal to one. Thus, each normalized component vector has a shape and a magnitude so that the components may be used as the basic building blocks of all light samples having those principal components. Accordingly, each light sample may be described in the following format by the combination of the normalized principal components multiplied by the appropriate scalar multipliers:

$$x_1 z_1 + x_2 z_2 + \ldots + x_n z_n.$$

The scalar multipliers $x_n$ may be considered the "magnitudes" of the principal components in a given light sample when the principal components are understood to have a standardized magnitude as provided by normalization.

Because the principal components are orthogonal, they may be used in a relatively straightforward mathematical procedure to decompose a light sample into the component magnitudes which accurately describe the data in the original sample. Since the original light sample may also be considered a vector in the multi-dimensional wavelength space, the dot product of the original signal vector with a principal component vector is the magnitude of the original signal in the direction of the normalized component vector. That is, it is the magnitude of the normalized principal component present in the original signal. This is analogous to breaking a vector in a three dimensional Cartesian space into its X, Y and Z components. The dot product of the three-dimensional vector with each axis vector, assuming each axis vector has a magnitude of 1, gives the magnitude of the three dimensional vector in each of the three directions. The dot product of the original signal and some other vector that is not perpendicular to the other three dimensions provides redundant data, since this magnitude is already contributed by two or more of the orthogonal axes.

Because the principal components are orthogonal, or perpendicular, to each other, the dot, or direct, product of any principal component with any other principal component is zero. Physically, this means that the components do not interfere with each other. If data is altered to change the magnitude of one component in the original light signal, the other components remain unchanged. In the analogous Cartesian example, reduction of the X component of the three dimensional vector does not affect the magnitudes of the Y and Z components.

Principal component analysis provides the fewest orthogonal components that can accurately describe the data carried by the light samples. Thus, in a mathematical sense, the principal components are components of the original light that do not interfere with each other and that represent the most compact description of the entire data carried by the light. Physically, each principal component is a light signal that forms a part of the original light signal. Each has a shape over some wavelength range within the original wavelength range. Summing the principal components produces the original signal, provided each component has the proper magnitude.

The principal components comprise a compression of the data carried by the total light signal. In a physical sense, the shape and wavelength range of the principal components describe what data is in the total light signal while the magnitude of each component describes how much of that data is there. If several light samples contain the same types of data, but in differing amounts, then a single set of principal components may be used to exactly describe (except for noise) each light sample by applying appropriate magnitudes to the components.

The principal components may be used to accurately estimate information carried by the light. For example, suppose samples of a certain brand of gasoline, when illuminated, produce light having the same principal components. Spreading each light sample with a spectrograph may produce wavelength spectra having shapes that vary from one gasoline sample to another. The differences may be due to any of several factors, for example differences in octane rating or lead content.

The differences in the sample spectra may be described as differences in the magnitudes of the principal components. For example, the gasoline samples might have four principal components. The magnitudes $x_n$ of these components in one sample might be J, K, L, and M, whereas in the next sample the magnitudes may be 0.94J, 1.07K, 1.13L and 0.86M. As noted above, once the principal components are determined, these magnitudes exactly describe their respective light samples.

Refineries desiring to periodically measure octane rating in their product may derive the octane information from the component magnitudes. Octane rating may be dependent upon data in more than one of the components. Octane rating may also be determined through conventional chemical analysis. Thus, if the component magnitudes and octane rating for each of several gasoline samples are measured, a multiple linear regression analysis may be performed for the component magnitudes against octane rating to provide an equation such as:

$$y=a_0+a_1x_1+a_2x_2+a_3x_3+a_4x_4 \quad \text{(Equation 2)},$$

where y is octane rating, $a_n$ are constants determined by the regression analysis, and $x_1$, $x_2$, $x_3$ and x4 are the first, second, third and fourth principal component magnitudes, respectively.

Using Equation 2, which may be referred to as a regression vector, refineries may accurately estimate octane rating of subsequent gasoline samples. Conventional systems perform regression vector calculations by computer, based on spectrograph measurements of the light sample by wavelength. The spectrograph system spreads the light sample into its spectrum and measures the intensity of the light at each wavelength over the spectrum wavelength range. If the regression vector in the Equation 2 form is used, the computer reads the intensity data and decomposes the light sample into the principal component magnitudes $x_n$ by determining the dot product of the total signal with each component. The component magnitudes are then applied to the regression equation to determine octane rating.

To simplify the procedure, however, the regression vector is typically converted to a form that is a function of wavelength so that only one dot product is performed. Each normalized principal component vector $z_n$ has a value over all or part of the total wavelength range. If each wavelength value of each component vector is multiplied by the regression constant $a_n$ corresponding to the component vector, and if the resulting weighted principal components are summed by wavelength, the regression vector takes the following form:

$$y=a_0+b_1u_1+b_2u_2+ \ldots +b_nu_n \quad \text{(Equation 3)},$$

where y is octane rating, $a_0$ is the first regression constant from Equation 2, $b_n$ is the sum of the multiple of each regression constant an from Equation 2 and the value of its respective normalized regression vector at wavelength n, and $u_n$ is the intensity of the light sample at wavelength n. Thus, the new constants define a vector in wavelength space that directly describes octane rating. The regression vector in a form as in Equation 3 represents the dot product of a light sample with this vector.

Normalization of the principal components provides the components with an arbitrary value for use during the regression analysis. Accordingly, it is very unlikely that the dot product result produced by the regression vector will be equal to the actual octane rating. The number will, however, be proportional to the octane rating. The proportionality factor may be determined by measuring octane rating of one or more samples by conventional means and comparing the result to the number produced by the regression vector. Thereafter, the computer can simply scale the dot product of the regression vector and spectrum to produce a number approximately equal to the octane rating.

An example of a conventional spectroscopy analysis system is provided in FIG. 2. A laser 20 directs light to a sample 22 by a bandpass filter 24, beam splitter 26, lens 28 and fiber optic cable 30. Light is reflected back through cable 30 through beam splitter 26 to a lens 32 to a spectrograph 34. Spectrograph 34 separates light from the illuminated sample by wavelength so that the intensity of the light at each wavelength can be measured by a detection device including a charge couple detector 36. Charge couple detector 36 is controlled by controller 38 and cooled by cooler 40. The detection device measures the light intensity of light from spectrograph 34 at each wavelength and outputs this data digitally to a computer 42, which stores the light intensity over the wavelength range. Computer 42 also stores a previously derived regression vector for the desired sample property, for example octane, and sums the multiple of the light intensity and the regression vector intensity at each wavelength over the sampled wavelength range, thereby obtaining the dot product of the light from the substance and the regression vector. Since this number is proportional to octane rating, the octane rating of the sample is identified.

Since the spectrograph separates the sample light into its wavelengths, a detector is needed that can detect and distinguish the relatively small amounts of light at each wavelength. Charge couple devices provide high sensitivity throughout the visible spectral region and into the near infrared with extremely low noise. These devices also provide high quantum efficiency, long lifetime, imaging capability and solid-state characteristics. Unfortunately, however, charge couple devices and their required operational instrumentation are very expensive. A typical instrument including such sensitive detectors, and the spectrographs needed for their operation, generally cost around $250,000. Furthermore, the devices are sensitive to environmental conditions. In a refinery, for example, they must be protected from explosion, vibration and temperature fluctuations and are often placed in protective housings approximately the size of a refrigerator. The total cost for these instruments may range from $200,000 to $500,000. The power requirements, cooling requirements, cost, complexity and maintenance requirements of these systems have made them impractical in many applications.

SUMMARY OF THE INVENTION

The present invention recognizes and addresses the foregoing disadvantages, and others, of prior art construction and methods.

Accordingly, it is an object of the present invention to provide an improved system for deriving information from light.

It is a further object of certain embodiments of the present invention to employ an optical filter mechanism to optically compress data carried by light into orthogonal components.

It is a still further object of certain embodiments of the present invention to optically compress data carried by light into components of the light so that data carried by said light may be measured by measuring a property of the components.

BRIEF DESCRIPTION OF THE DRAWINGS

A full and enabling disclosure of the present invention, including the best mode thereof, directed to one of ordinary skill in the art, is set forth in the specification, which makes reference to the appended drawings, in which:

FIG. 8A is a schematic illustration of an optical fiber splitter mechanism for directing light from a sample to dual filters for separately weighting positive and negative regression vector portions;

FIG. 8B is a schematic illustration of a beam splitter for directing light from a sample to dual filters for separately weighting positive and negative regression vector portions;

FIG. 8C is a schematic illustration of dual filters disposed to separately weight positive and negative regression vector portions;

FIG. 14 is a schematic illustration of an embodiment of an optical filter according to the present invention FIG. 15 is a schematic illustration of an optical analysis system according to the present invention;

Figure 1:
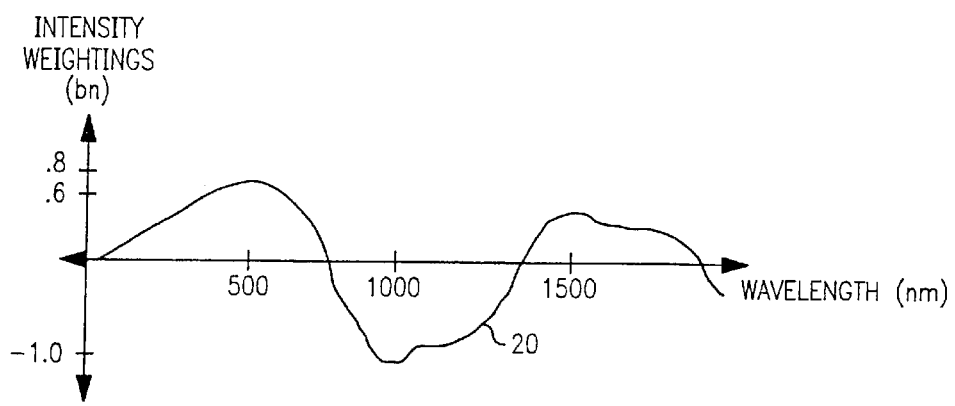
FIG. 1 is a graphical representation of an exemplary spectroscopic regression vector.
Figure 2:
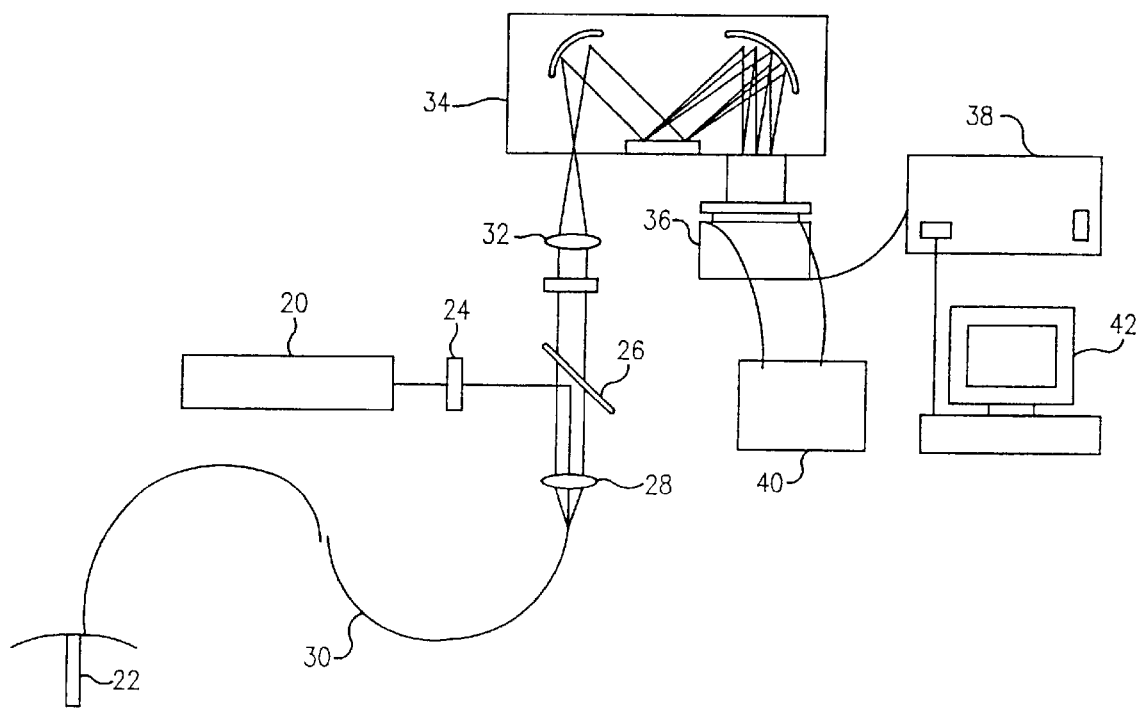
FIG. 2 is a schematic representation of a prior art spectroscopy analysis system.

Repeat use of reference characters in the present specification and drawings is intended to represent same or analogous features or elements of the invention.

DETAILED DESCRIPTION OF THE PREFERRED EMBODIMENTS

Reference will now be made in detail to presently preferred embodiments of the invention, one or more examples of which are illustrated in the accompanying drawings. Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the invention.

Figure 3A:
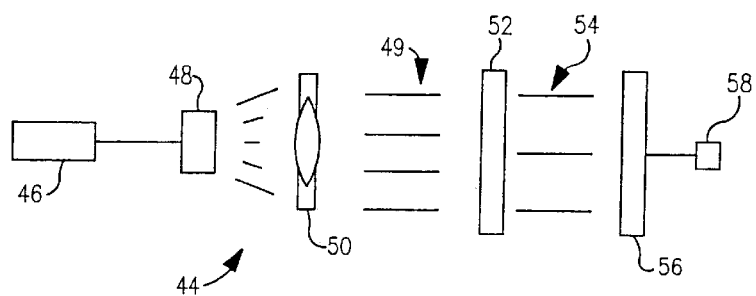
FIG. 3A is a schematic illustration of an optical analysis system according to the present invention.

In one presently preferred embodiment of an optical analysis system, shown generally at 44 in FIG. 3A, an energy source 46 illuminates a sample substance 48. Light passing through or reflected from sample 48 is collimated by collimator 50, which includes one or more lenses or mirrors to focus light from sample 48 into a parallel beam 49. Light from collimator 50 is conveyed, for example through air, fiber optic cable, or other suitable medium, to optical filter 52. Optical filter 52 is an interference device. That is, its performance depends upon the path that light takes through it. Thus, collimator 50 directs a parallel beam 49 to the filter. Light may be directed through a bandpass filter prior to optical filter 52 to eliminate light at wavelengths other than those encompassed by the regression vector.

Collimator 50 is not a spectrograph. Thus, the light in light beam 49 is unseparated, multiple wavelength light. Filter 52, however, is a wavelength-specific light intensity filter. That is, the weighting it applies to the light varies by wavelength. For example, suppose a light beam includes light at two wavelengths, 500 nm and 1000 nm, and that the light intensity at 500 nm is G and the light intensity at 1000 nm is H. The total light intensity is G+H. A filter such as filter 52 may be configured to simultaneously filter the 500 nm light by 50% and the 1000 nm light by 75%, even though the light at the two wavelengths are combined parts of the same light beam. Accordingly, a light intensity detector measuring the output of the filter would measure an intensity of 0.5G+0.75H.

In one preferred embodiment, an optical filter 52 includes multiple layers of materials having different refractive indices. By properly selecting the materials and designing the layer spacings, the filter can be made to selectively pass predetermined fractions of light at different wavelengths. Once the desired weighting at each wavelength is determined, the materials and spacings that compose optical filter 52 may be determined using a variety of approximation methods. These methods include, for example, determining the inverse Fourier transform (IFT) of the optical transmission spectrum and structuring the filter as the physical representation of the IFT. The IFT suggests a continuous variation of the refractive index within the filter structure. At present, however, Applicants are unaware of a process for producing such a continuously varying filter, and, therefore, further approximations are used to convert the IFT into a usable structure based on known materials with constant refractive indices. Such filters may be obtained through the research group including George Dobrolski and Pierre Verly under the National Research Council of Canada. Information regarding the structure of such filters is provided at Applied Optics, Vol. 35, pp. 5484–5492 (1996) and Vol. 29, pp. 2876–2893 (1990).

In another preferred embodiment, a direct iterative process known as the "needle" method is used to construct the filter. This method begins with the refractive indices of known materials and an estimate of the filter thickness. Through a computer algorithm, the effect of inserting "needles" of a second material into a first material is estimated. These needles are then moved around within the second material, using the interference pattern they create as a guide, until a best approximation of the desired interference pattern is produced. It should be understood that other suitable iterative methods may be used to produce the filter.

In one preferred embodiment of the present invention, the weightings that filter 52 applies at each wavelength are set to the regression weightings $b_n$ described with respect to Equation 3 in the Background of the Invention. Thus, optical filter 52 optically performs the dot product of light beam 49 and a desired regression vector, and the intensity of light 54 output from optical filter 52 is directly related to the desired information. For example, if sample 48 is a gasoline sample, and if the regression vector embodied by filter 52 is an octane regression vector for that particular gasoline type, the intensity of light 54 is directly related to the octane of sample 48.

Accordingly, filter 52 simultaneously and optically performs two spectroscopic analysis steps. First, it compresses data carried by light 49 into orthogonal components. Second, it weights the orthogonal component magnitudes by regression vector weightings so that the output of the filter is directly related to desired information.

Although, as discussed in more detail below, various types of orthogonal components may be used, the orthogonal components in the octane example may be assumed to be principal components since the light characteristics of the light source, the illuminated gasoline sample 48, are known. Since gasoline samples 48 measured by system 44 are similar, the regression constants $a_n$ as in Equation 2 may be calculated and combined to determine regression constants $b_n$ as in Equation 3. Thus, optical filter 52 performs the dot product of the light 49 and the regression vector.

A detector 56 receives weighted light 54 from filter 52 and measures its intensity. The measured intensity is the sum of the intensity at each wavelength of light 54. As noted above, the intensity of light 54 is directly related to the actual measurement of the information associated with the regression vector. If the regression vector includes an offset value $a_o$ as in Equation 3, this may be introduced by a processor 58 which receives the output from detector 56. The processor may also scale the output, to account for normalization of the orthogonal components used to derive the regression vector as described above, so that the final output reflects an actual measurement of the desired information. The scaling may also be performed by one or more amplifiers following the detector, by an optical filter between filter 52 and detector 56, or by filter 52 if the scaling factor is incorporated into the wavelength weightings. Processor 58 may be a stand-alone device or may be incorporated by the detector. It may comprise a microprocessor, for example in a stand-alone computer, or digital and/or analog circuitry. It may also include a display meter to display the detector output in a modified or unmodified form and/or an output device so that the detector output may be directed to external systems for processing. Where there is no offset $a_0$, or where all scaling is to be performed by an external system, the processor 58 may consist solely of a display meter and/or output device.

As noted above, detector 56 may be a conventional light detector, for example constructed from germanium or silicon, for measuring the intensity of incident light. It should be understood, however, that any other suitable light detector devices may be used, for example including cameras or other film devices.

Figure 3B:
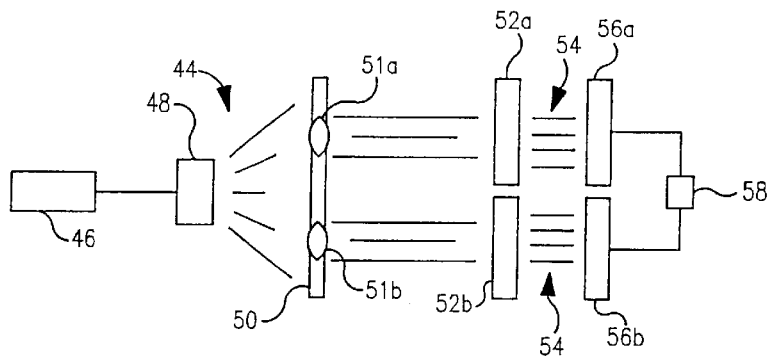
FIG. 3B is a schematic illustration of an optical analysis system according to the present invention.
Figure 3C:
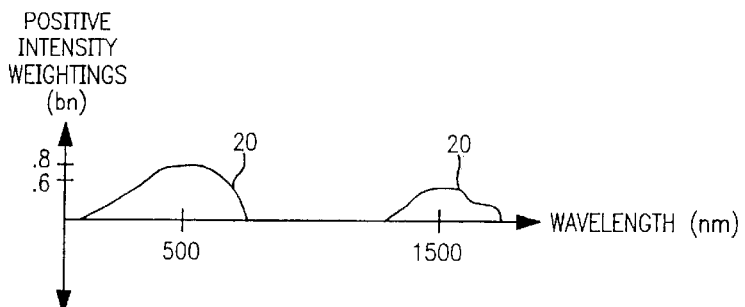
FIG. 3C is a graphical representation of the positive component of the spectroscopic regression vector as in FIG. 1.
Figure 3D:
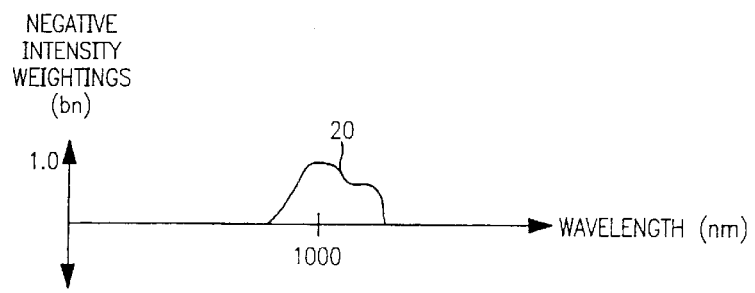
FIG. 3D is a graphical representation of the negative component of the spectroscopic regression vector as in FIG. 1.

FIG. 3A illustrates a single optical filter 52. Since the optical filter of this embodiment is a transmission filter which passes a certain percentage of incident light at each wavelength, it is unable to apply negative weightings. It is very unlikely, however, that the regression vector will be entirely positive. That is, it is unlikely that each regression constant $b_n$ will be positive. To account for positive and negative constants $b_n$ of an exemplary regression vector 20 as in FIG. 1, a system as illustrated in FIG. 3B includes a collimator 50 including a pair of collimating lenses 51a and 51b directing light to filter devices 52a and 52b, respectively. Filter 52a is weighted with the positive portion of the regression vector 20 (FIG. 1) as shown in FIG. 3C, and filter 52b is weighted with the negative portion as illustrated as in FIG. 3D. A pair of detectors 56a and 56b receive the output light 54 from filter 52a and 52b, respectively. Processor 58 sums the positive output from detector 56a with the negative output from detector 56b to provide the dot product of the regression vector and the light from sample 48. It should be understood that the output of detector 56b is positive but that the output is summed to the detector 56a output as a negative number. That is, processor 58 subtracts the output of detector 56b from the output of detector 56a.

The regression vector constants $b_n$ are most likely between −1 and 1 and are likely to be relatively close to 0. Since, in the embodiment of optical filter 52 illustrated in FIGS. 3A and 3B, these numbers represent percentages of incident light passed to the detectors, the signal-to-noise ratio may be improved by unitizing the regression vector constants. That is, the constant $b_n$ having the largest absolute value is scaled to 1 or −1, depending on whether the constant is positive or negative. All the other constants $b_n$ are scaled by the same factor. These scaled constants then become the weightings $b_n$ by which filter 52 weights incident light at each wavelength. The output from the filter is then reduced by this scaling factor in the manner described above regarding the scaling factor caused by the use of normalized orthogonal components. That is, the regression vector's unitization modifies the scaling factor resulting from regression vector normalization.

Although unlikely, it is possible that one or more of the constants $b_n$ of Equation 3 may be greater than 1 or less than −1. Although it is possible to use optical filter mechanisms, such as are described below, which are able to amplify light at different wavelengths, a scaling factor less than 1 may be used to reduce the constant $b_n$ so that the greatest magnitude constant is 1 or −1. The unitized constants may then be used by an optical filter such as filter 52 described above.

Figure 7A:
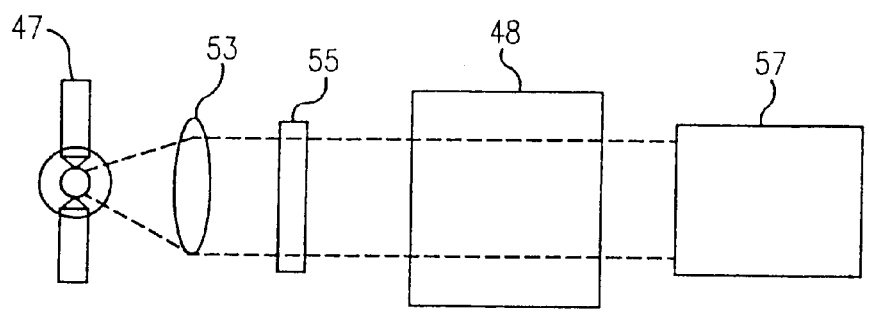
FIG. 7A is a schematic illustration of the present invention utilizing an absorption spectroscopy method.

Those of ordinary skill in this art should understand that energy source 46 may include various suitable energy sources, for example as are used in known spectroscopy methods. For example, referring to FIG. 7A, energy source 46 may include a broad band light source 47 proximate sample 48. Exemplary broad band light sources include lamps, filaments, LEDs, or other devices providing multi-wavelength light substantially over the visible and near visible light spectrum. One or more broad band sources may be positioned proximate sample 48 so that light emanating from the light source is directed by lens 53 to bandpass filter 55, which limits the light to a wavelength range equal to or within the regression vector wavelength range, and then on to the sample. This light may then pass through, as shown in FIG. 7A, or reflect from the sample to be analyzed downstream by optical system 57 to derive desired information about the sample. Optical system 57 includes an optical filter mechanism such as illustrated in FIG. 3B. Examples of such absorbance spectroscopy methods include infrared absorbance, near infrared absorbance (NIR), mid infrared absorbance (MIR) and ultraviolet visible absorbance (UV-VIS).

Energy source 46 may also illuminate sample 48 by exciting the sample so that it emits light. Such energy sources may include lasers, lamps or electricity sources. For example, referring to FIG. 7B, a laser or lamp 47 emits light that is filtered and directed to sample 48 by lenses 53a and 53b and bandpass filter 55. Sample 48 is excited so that it emits light, which is directed by lens 53c to system 57 for further analysis. Examples of such spectroscopy methods include fluorescence emission, phosphorescence emission, luminescence emission and electroluminescence.

Figure 7B:
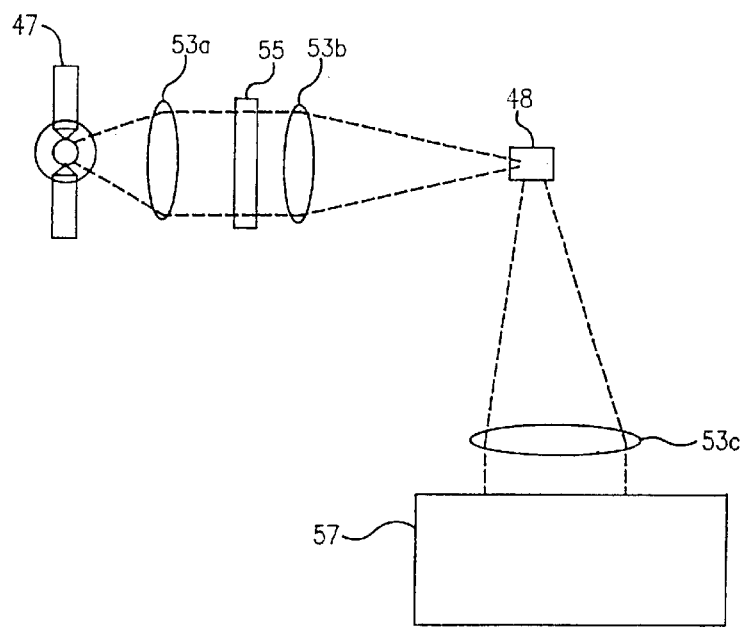
FIG. 7B is a schematic illustration of the present invention utilizing an emission or a scattering spectroscopy method.

FIG. 7B may also be used to illustrate scattering methods in which energy source 46, which typically includes a laser 47, exposes sample 48 to monochromatic light. As light passes through the sample, it is scattered into various wavelength bands. Examples of such methods include Raman scattering, Mie scattering, Rayleigh scattering and quasi-elastic light scattering. The configuration illustrated in FIG. 7B may be used in both emission methods and scattering methods, primarily because luminescence and scattering effects normally coexist, and the difference between these method types is largely a matter of analyzing the output. Certain circumstances, for example the wavelength of the energy used to illuminate the sample, or the sample itself, may cause one effect to dominate ever the other.

It should be understood that any of the above-described, or other suitable illumination methods may be employed with the present invention. Those of ordinary skill in this art should understand such methods and systems, and further detailed explanation thereof is therefore not provided.

Figure 7C:
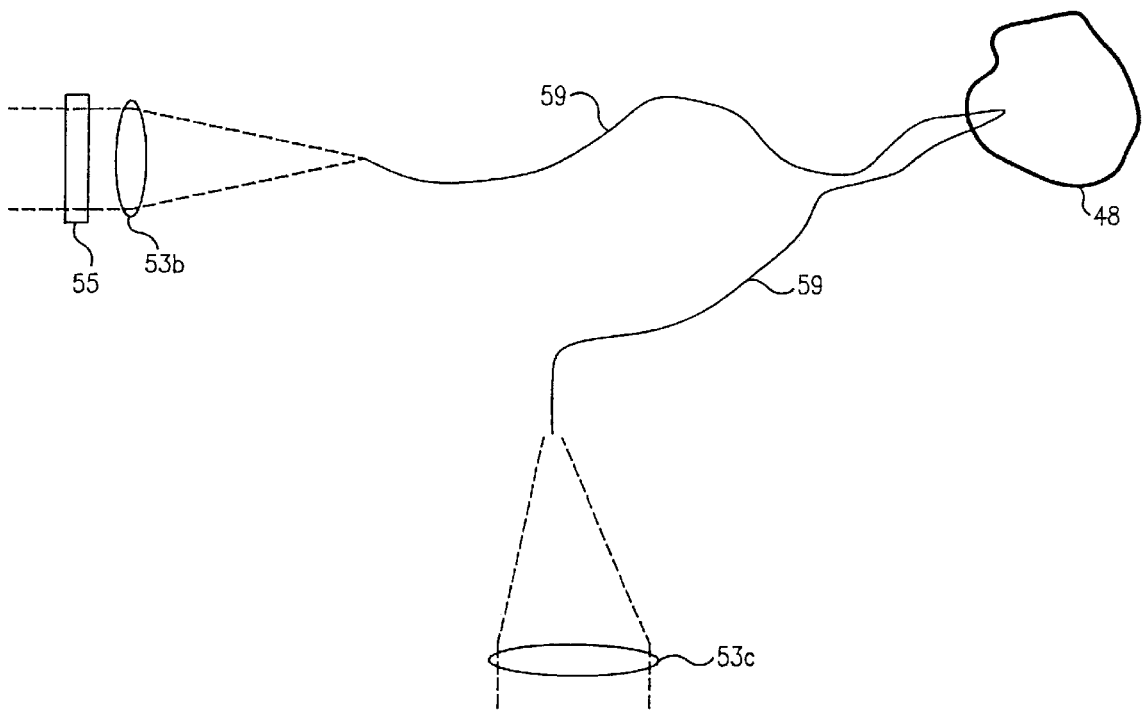
FIG. 7C is a partial schematic illustration of the present invention wherein light is directed to and from a sampled substance over optical fiber.

In the examples illustrated in FIGS. 7A and 7B, light is conveyed to and from sample 48 over air. It should be understood, however, that other light media may be used, for example fiber optic elements 59 as illustrated in FIG. 7C.

A spectroscopic regression vector is affected by the instruments and methods used to drive it. Thus, once a regression vector has been established with certain equipment, an equipment change may require a calibration of the system. To effect a calibration without recalculating the regression vector, filters may be placed between the filters 52a, 52b and detectors 56a, 56b shown in FIG. 3B. Alternatively, adjustable amplifiers may adjust the detector output, or processor 58 may be reprogrammed or recalibrated.

Calibration, and other system adjustments, may be easily effected where the system is configured to execute the regression vector equation as in Equation 2. A series of optical filter pairs, such as filters 52a and 52b in FIG. 3B, may be used to separate the orthogonal components from the light sample. Amplifiers may then apply the regression components $a_n$ as in Equation 2 to the output of the detectors following each optical filter pair. If the amplifiers are adjustable, the regression vector constants may be adjusted directly to account for the calibration. This type of arrangement may also be used where a product change requires redetermination of the regression vector. For example, a change in a refinery's manufacturing process or ambient conditions may change the regression vector. The adjustable amplifiers permit the change without requiring new optical filters. While the Equation 2 arrangement requires more filters than the Equation 3 arrangement, the expense may be justified if the regression vector is likely to change. A more detailed description of an Equation 2 arrangement is provided below.

It should also be understood that the shape and magnitude of the regression vector will depend upon the method used to derive it. For example, in terms of frequency, Raman spectroscopy produces sharp (for example, 10 cm$^{-1}$) peaks, while near infrared spectroscopy produces broader (for example 100 cm$^{-1}$) peaks, and UV-VIS spectroscopy produces very broad (for example, 500 cm$^{-1}$) peaks. Thus, the wavelength distribution is different for the different types of spectroscopy. Although the magnitudes may differ, all regression vectors may be scaled to unit weightings, for example through appropriate filter configuration. As noted above, subsequent electronics may provide correction via an amplifier or other suitable device. Although it may be possible to use different spectroscopy methods in deriving the regression vector and in performing the subsequent analysis if the filter is properly configured to account for the difference, it is preferred to use the same spectroscopy method for both.

Light from sample 48 may be directed to lenses 51a and 51b by any of several suitable methods. Referring to FIG. 8A, for example, light may be conducted from the sample to the lenses 51a and 51b over fiber optic cable 80 constructed in a bundle branching into two sections. Light striking the combined face of the fiber bundle is separated into two divisions 80a and 80b which approach the lenses. Alternatively, referring to FIG. 8B, a beam splitter 82 may be used to separate the light, as should be understood by those of ordinary skill in this art. The beam splitter assembly could be neutral, splitting every wavelength nearly equally into two directions, or dichroic, sending some wavelengths in one direction and others in another. In another configuration, light is split by the disposition of the filters 52 rather than by an upstream device. Thus, a single lens collimator 50 is used to direct light from the sample to the filters.

The first of the filters, for example filter 52a in FIG. 8C, is disposed to operate at a slight angle, for example 10°, with respect to the path of light 49. Detector 56a (not shown in FIG. 8C) is disposed beyond filter 52a to receive the light transmitted by the filter. The light of all wavelengths not passed by filter 52a is reflected at an angle of 20° from the path of light 49. Filter 52b is disposed to operatively receive this light, and detector 56b (not shown in FIG. 8C) is disposed beyond filter 52b to receive the weighted light therefrom. Processor 58 (not shown in FIG. 8C) measures the output of the two detectors as described above. Since filters 52a and 52b never have overlapping transmission, the reflected light from the first can feed the second filter directly, obviating the need to separate the light prior to filtering.

Figure 6:
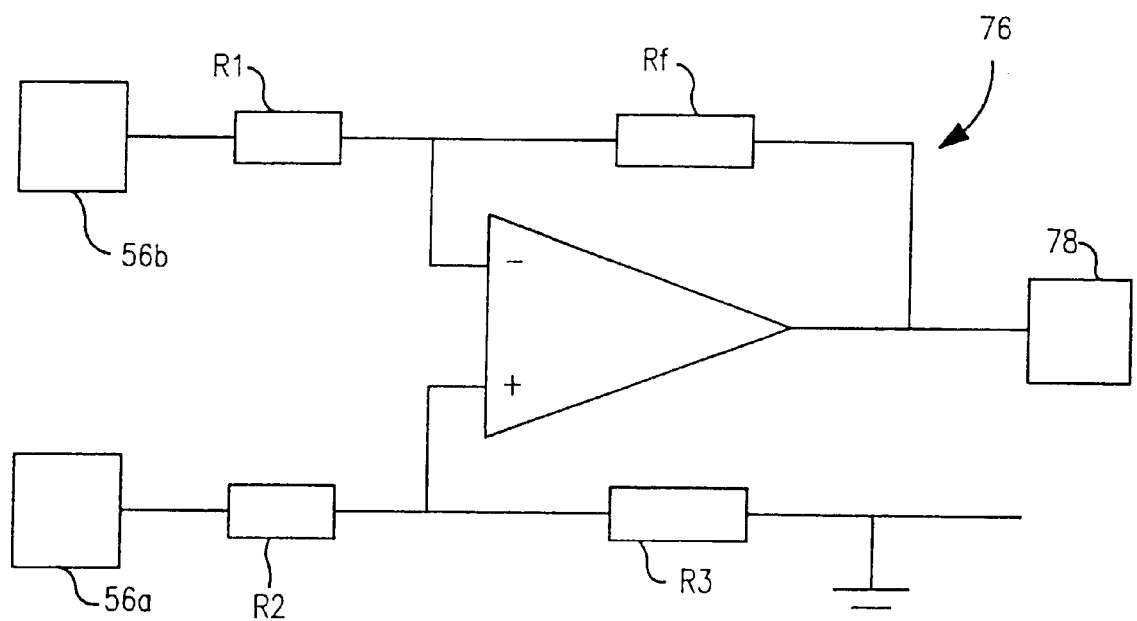
FIG. 6 is a schematic illustration of a summing circuit for summing weighted positive and negative light component portions.

One exemplary embodiment of processor 58 is schematically illustrated in FIG. 6. Output signals from detector 56a and 56b are provided to a resistor and op-amp circuit 76. Since the outputs from the detectors are positive, the summing circuit performs a subtraction function. Specifically, the output to display device 78 is given by the equation $v_o=(R3/R1)((R1+Rf)/(R2+R3))56a-(Rf/R1)56b$. By appropriately selecting the resistor values, the amplifier gains, if different, can be compensated and the correct substraction performed.

Various suitable filter mechanisms other than the filter devices described above with respect to FIG. 3B may be used for optical data compression. Although the discussion below provides examples of such mechanisms in the context of an Equation 3-type regression vector arrangement, it should be understood that such mechanisms may be applied in other embodiments described herein.

Figure 4A:
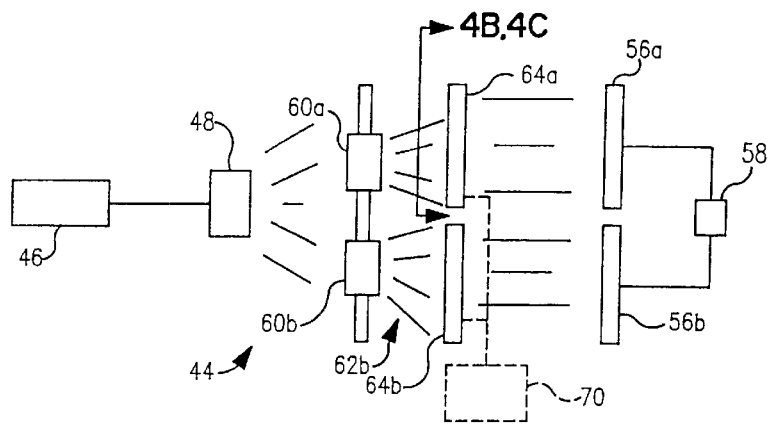
FIG. 4A is a schematic illustration of an optical analysis system according to the present invention.

Accordingly, in the embodiment illustrated in FIG. 4A, an optical filter mechanism includes a pair of spectrographs 60a and 60b and a pair of optical filters 64a and 64b. Light from sample 48 is directed to spectrographs 60a and 60b, which output light spectra 62a and 62b to the filters. The operation and construction of a spectrograph should be well known to those of ordinary skill in this art and are, therefore, not described in detail herein. In general, however, each spectrograph includes a narrow input slit of a given height and produces an output spectrum much broader than the input slit but having the same height. The light intensity varies laterally across the spectrum by light wavelength.

Figure 4B:
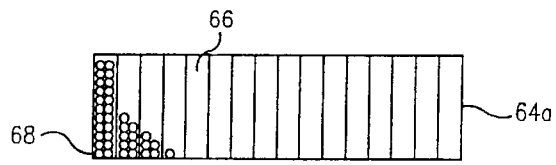
FIG. 4B is a schematic illustration of an exemplary filter device for use in the system as in FIG. 4A.

As discussed above regarding the system illustrated in FIG. 3B, the system of FIG. 4A separately weights the positive and negative regression vector constants. Thus, the system includes two filters 64a and 64b, weighted with the positive and negative constants, respectively. Although configured to the different weightings, the structure and general operation of the two filters is the same. Accordingly, only filter 64a is illustrated in FIG. 4B. Referring to FIG. 4B, filter device 64a includes a plurality of areas 66 arranged so that each area 66 receives light of a particular wavelength in spectrum 62a. Since areas 66 have a certain width, each receives light from spectrum 62a over a certain wavelength range. However, the range is small and may be considered a single wavelength as used herein.

The total spectrum wavelength range depends, for example, on the spectroscopy method used. For example, Raman typically covers a more narrow range than NIR. Also, some sections of the optical spectrum may contain more information than other sections. Thus, some spectrum sections may be omitted from the regression vector to improve performance.

Filter device 64a weights the intensity of light at each wavelength in spectrum 62a as determined by the spectroscopic regression vector. The weightings may be effected in various suitable fashions. For example, each area 66 may include a plurality of light sensor devices 68, for example including liquid crystal display devices (LCDs) or fiber optic elements. Each device 68 detects the presence or absence of incident light. Thus, the weighting at any given area 66 may be determined by selecting the number of devices 68 which will be measured. For example, a certain number of devices 68 may be deactivated, or a control system may selectively monitor the output of a predetermined number of the devices. Weighting may also be accomplished by selecting the density of the sensor devices 68 over the various wavelengths. Again, the weightings at a given "wavelength" will be applied over a certain range. For example, since fiber optic elements are approximately 0.3 nm wide in wavelength space, the wavelength range of a particular area is approximately 0.3 nm.

Filter 64a and an associated control system may comprise a single unit which weights light from spectrograph 60 and detects the weighted light. Such a control system may include a computer device 70 for controlling the operation of the filters and monitoring their output.

Figure 4C:
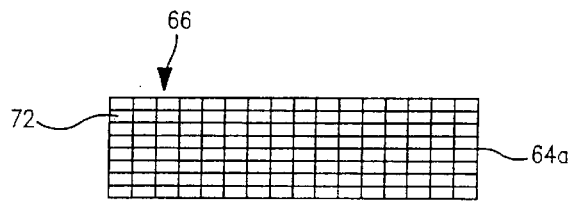
FIG. 4C is a schematic illustration of an exemplary filter device for use in the system as in FIG. 4A.

In another preferred embodiment, filter devices 64a and 64b may each include an array of transmission filters configured to selectively pass light to detector devices 56a and 56b, respectively. Referring to FIG. 4C, each area 66 of filter 64a includes a plurality of transmission filters 72 so that the amount of light measured by detector 56a at each wavelength along the spectrum 62a is determined by the number of transmission filters which pass light at each area 66. The number of transmission filters passing light at each area is determined by the weightings of the regression vector. The filters 72 may include, for example, adjustable shutters which may be selectively opened or closed. Thus, the number of open or closed shutters in a given area 66 determines the percentage of light passed from that area to the detector 56a.

Alternatively, filters 72 may be constructed so that each passes a predetermined percentage of incident light, thereby causing the area 66 to pass a predetermined percentage. By including the proper such filters, which may include, for example, photographic film plates or holographic optical elements, the light passing percentages at each area 66 may be set to the regression vector weighting at the relevant wavelength.

Filters 64a in FIGS. 4B and 4C may be adjustable so that the weightings at each wavelength may be changed to accommodate a new regression vector. For example, a number of sensors 68 may be selectively activated, deactivated or monitored as needed, for example by computer device 70. Similarly, transmission filters 72 may be activated, deactivated or otherwise configured, for example manually or by computer 70, to pass or reject light as needed.

Figure 5:
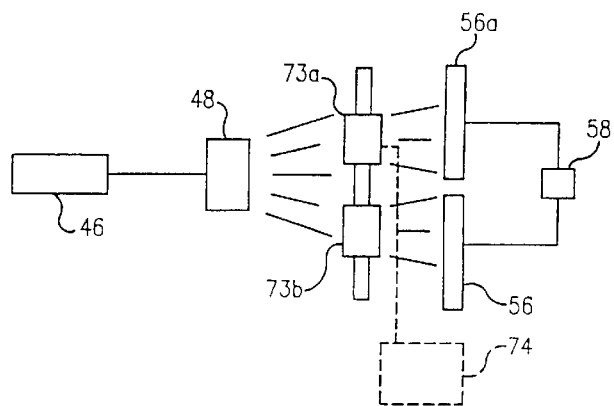
FIG. 5 is a schematic illustration of an optical analysis system according to the present invention.

In another preferred embodiment illustrated in FIG. 5, light from sample 48 is weighted by acoustooptical filters 73a and 73b. Again, two filters are used to accommodate positive and negative regression vector constants. Each filter 73a and 73b passes light at a single wavelength at a time, the wavelength being determined by acoustic wave control signals from computer 74. The filters weight the light from sample 48 by varying the time over which light is passed at each wavelength. By setting the relative time periods at each wavelength to correspond to the relative weightings at each wavelength in the regression vector, the filters weight the light in a pattern that corresponds to the regression vector. Light detector devices 56a and 56b measure the intensity of light passed from filters 73a and 73b as they scan through the applicable wavelength range. Processor 58 sums the positive component from detector 56a with the negative component of detector 56b. Alternatively, filters 73a and 73b may be liquid crystal tunable filters. The operation of crystal tunable filters, as should be understood by those of ordinary skill in this art, is similar to that of acoustooptical filters.

While the acoustooptical filters are described above as passing light at a particular wavelength, it should be understood that light is passed over a relatively small wavelength range. For example, an acoustooptical filter may have a bandwidth near 10 nm. As discussed herein, however, these ranges may be considered single wavelengths for a given application.

While the embodiments of the present invention discussed above weight the intensity or, similarly, time of light intensity exposure of light from the sample substance, it should be understood that other properties of light may be weighted. For example, light polarization or coherence may be weighted as a function of wavelength.

The present invention may be used to optically compress light data in applications in which the regression vector constants may change from sample to sample and in applications not suitable for principal component analysis. For example, a class of substances may produce the same principal components but not be subject to a unique regression vector. Gasolines again provide an example. All gasolines are composed of the same major compounds, but a high octane gasoline may be obtained in various ways by mixing different compounds. Particularly, mixtures may vary from manufacturer to manufacturer. Principal component analysis performed on sample gasoline spectra from different manufacturers may reveal that the gasolines have the same, or very similar, principal components but that the relative importance of the components differs among the manufacturers. Consequently, the regression vector of the gasoline of one manufacturer will be different from that of another. Another example is the prediction of blood glucose levels using light transmitted through blood samples. A regression vector may be determined for an individual to relate the blood principal components to blood glucose level. From this point on, this persons blood glucose level may be monitored optically. If the same instrument is used on another person, however, the glucose measurement may fail, even though the principal components for the two individuals are the same. Differences between the individuals, for example race, blood type, or weight, may cause the weightings of the principal components to differ so significantly that the regression vector for the first individual is not applicable to the second.

Figure 9:
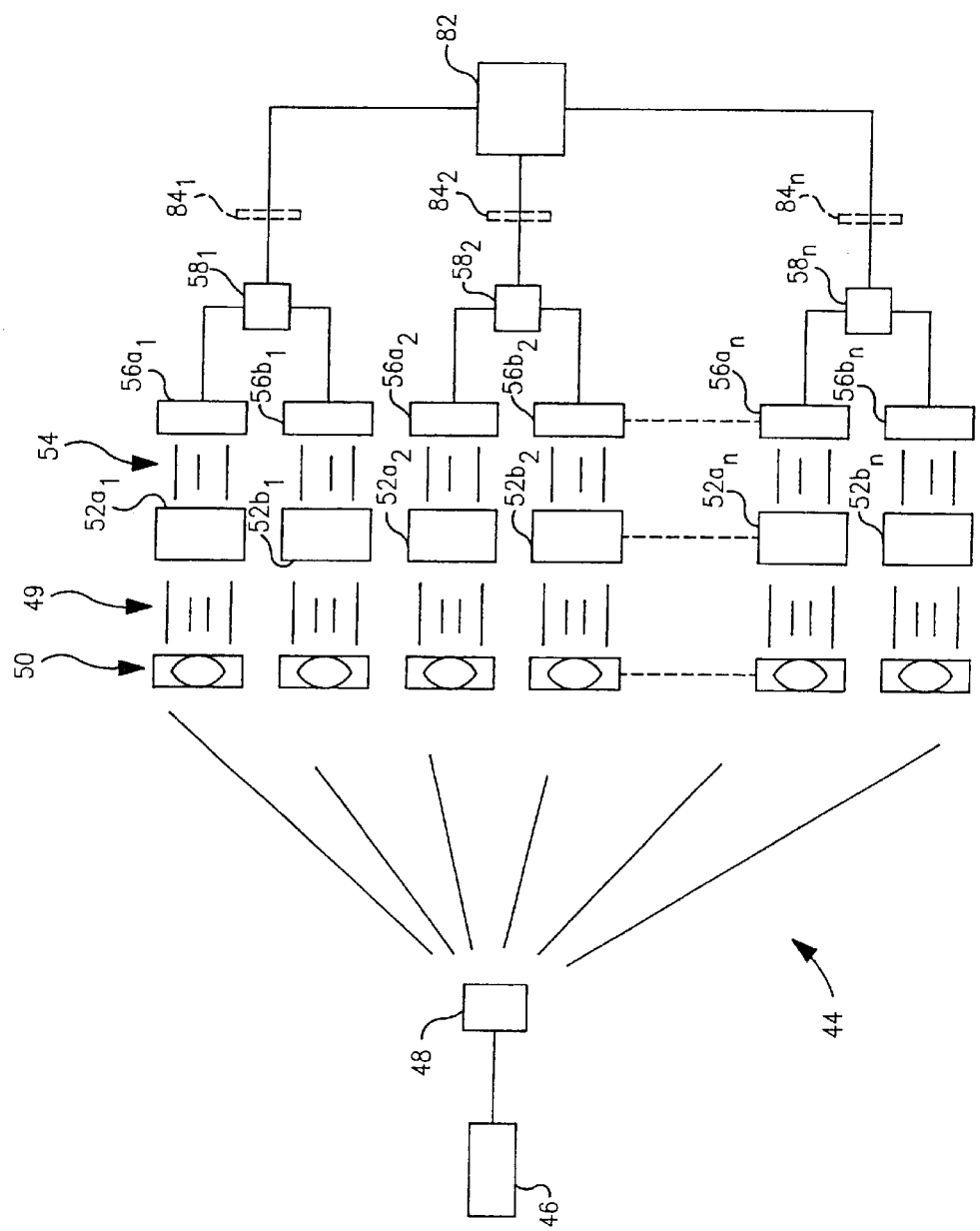
FIG. 9 is a schematic illustration of an optical analysis system according to the present invention.

An optical analysis system 44 illustrated in FIG. 9 may be effectively used in these situations to optically compress light data from non-similar light sources to derive desired information. An energy source 46 illuminates a sample, for example a blood sample, 48 by any suitable method as described above. Light from illuminated sample 48 is conveyed by suitable means to a series of collimators 50 which direct the light in parallel beams 49 to a series of optical filter devices. The optical filters may be constructed, for example, as the optical filters 52a and 52b discussed above regarding FIG. 3B. The optical filters are grouped in pairs, each pair corresponding to a principal component applicable to the sample, in this case human blood. Thus, optical filters $52a_1$ and $52b_1$ may correspond to the positive and negative portions, respectively, of the first principal component. Optical filters $52a_2$ and $52b_2$ correspond to the second principal component. Additional filter pairs follow up to filters $52a_n$ and $52b_n$, where n is the number of principal components.

The arrangement as in FIG. 9 may be used to derive information from a light sample using the regression vector format as in Equation 2. Since a regression vector for one sample is inapplicable to other samples, there are no regression constants $a_1$ through $a_n$ that can be used for each blood sample. Thus, in constructing the optical filters, these constants are assumed to be 1. The optical filter weighting percentages, therefore, correspond to the values of the normalized principal components at each wavelength. For example, the normalized first principal component may have a value of −0.04 at 500 nm. Thus, the weighting percentage of optical filter $52b_1$ at 500 nm is 4%, and the weighting of optical filter $52a_1$ at the same wavelength is 0. The components may also be unitized to improve the signal-to-noise ratio. Accordingly, each optical filter pair performs the dot product of the light from the light source with its respective principal component vector, and the amount of light output from the optical filter pair is proportional to the contribution of that principal component to the original light from the sample. Again, the proportionality is due to the normalization and unitization of the component vector. This may be accounted for by processor 58, which sums the output of the light detectors 56a and 56b or by a downstream computing device 82.

The optical filter mechanism of FIG. 9 compresses the data carried by the light from the light source into principal components in a manner so that the principal component magnitudes may be separately detected. Accordingly, a display device such as an LED (not shown) may be attached to the output of each processor 58. Assuming that the proportionality for each component is accounted for in some manner prior to the processor output, such devices display the magnitude of each component in the original light.

This system may be used to accurately measure the blood glucose level of any individual. For example, several blood samples may be drawn from an individual and analyzed by the system to determine the magnitude of each principal component in each sample. This data may be directed to a computer 82, or other suitable device, which performs a multiple linear regression of the component magnitudes for each sample against the blood glucose level for each sample measured by conventional means. The regression produces the regression constants $a_0$ through $a_n$ of Equation 2. The constants may be applied to the output from subsequent blood samples by computer 82 so that the system may be used to accurately measure blood glucose for this individual.

In another embodiment, computer 82 is not used in measuring subsequent blood samples. Instead, a series of adjustable amplifiers 84 apply a gain to the detector outputs equal to the respective regression constants $a_1$ through $a_n$. A summing circuit, which may include any suitable mechanism such as a microprocessor or summing circuitry, may be used to sum the output of each amplifier 84. The output of the summing device may then be offset by the constant $a_0$ and scaled by a scaling factor as described above by an appropriate amplifier or computing device. The offset mechanism may be any suitable device which, for example, adds or subtracts an appropriate DC offset to or from the detector output. The offset mechanism and the scaling factor amplifier may also be adjustable.

Accordingly, the system as in FIG. 9 may be used to analyze any sample having the principal components embodied by the optical filters. It may be used to determine the regression vector constants for similar samples and thereafter, by appropriately setting the adjustable gains and offset, to apply the appropriate regression vector for those samples. Such a system may also be used where a regression vector is known to change over time. Thus, rather than constructing a single optical filter pair to perform the dot product according to the Equation 3 regression vector, a refinery may use an adjustable configuration as shown in FIG. 9 so that the regression vector may be changed as needed.

It should also be understood that the system illustrated in FIG. 9 may be constructed in various suitable forms. For example, various suitable combinations of computing devices and/or amplifiers and/or optical filters may be used to effect the gains, offsets and summations applied and performed by the system. For example, the detector outputs may all be directed to a computer which may perform all of these functions. Furthermore, the system may be packaged in a relatively small kit with an energy source capable of illuminating a blood sample so that, once the appropriate gains and offset are set, an individual may perform glucose testing at home. Principal components are merely one set of orthogonal components. They are very useful in that they represent the most compact form of data compression. That is, they represent the fewest number of orthogonal components that completely describe the data in the original signal. If light is to be analyzed from sources having different principal components, however, principal component analysis is not an effective data compression tool. Thus, it should be understood that the filter mechanism of the present invention may compress light data into orthogonal components other than principal components, for example Fourier components or wavelet components. Like principal components, these other component types are orthogonal components of the original waveform. They are not, however, as efficient as principal components, and more components are necessary to adequately describe the light data. For example, each Fourier component has the shape of a sine wave. Thus, the Fourier components are a series of sine waves of different magnitudes and frequencies which, when combined, produce the original signal. Each sine shape may be normalized and/or unitized so that each component may be used as weightings for an optical filter pair such as filters $52a_1$ and $52b_1$ in FIG. 9. Thus, the system in FIG. 9 could be configured to compress the light data into Fourier components.

Embodiments of the present invention using non-principal component data compression may be used in a variety of applications. For example, the present invention may be used with satellite systems that receive light reflected from the earth and relay light data to the earth for analysis to derive desired information, for example the location of oil deposits. In this case, the light source is light reflected from earth rather than light from an illuminated sample substance. Light reflected from different parts of the earth may have very different principal components, but may still be affected by oil deposits beneath the surface. A series of optical filters may be constructed to compress the data carried by this light into a predetermined set of orthogonal components, for example Fourier or wavelength components. An optical filter pair, such as illustrated in FIG. 9, may be constructed for each component and housed in the satellite. The earth's surface may be imaged through each filter pair in turn to provide a compact data set containing all the pertinent spectroscopic data that can be obtained. Thus, the satellite carries an optical filter for each significant component and, for example, a separate camera for each optical filter or one camera that sequentially views the earth's surface through each filter. This compact information may be transmitted to a processing unit on earth, where the spectra can be reconstituted from the compact representation of Fourier or wavelet components. The number of components used may be chosen to provide a desired spectroscopic resolution. That is, the more components used, the more accurately the actual spectrum may be recreated. Thus, earth-based researchers may have at their disposal all the significant optical information about the earth's surface.

The present invention may also be used in systems such as communication systems where information is stored in predetermined orthogonal components. Light comprising the components is transmitted through an optical medium to a set of filters configured to compress the light to the components to derive the information. By using orthogonal components, multiple signals may be transmitted simultaneously without interference.

Such a system is particularly advantageous in long range optical communications systems that transmit information in wavelength-division multiplexing (WDM).

In current communications systems, the use of WDM is limited by overlap of neighboring wavelength channels. For example, if the closest spacing of WDM channels without overlap is 10 nm, and if the wavelength band is approximately 100 nm, at most 10 channels may be simultaneously transmitted. Using the present invention, a far greater number of channels may be arranged as orthogonal components in wavelength space and combined to be simultaneously transmitted over an optical medium, at the end of which a group of optical filters compresses the data into the orthogonal components for measurement. Channel overlap does not damage data transmission integrity because the channels are orthogonal to one another.

In one preferred embodiment, each channel takes the form of some predefined signal, for example a pulse having some shape. The pulses are orthogonal to each other. To create orthogonal pulses, each pulse is configured so that if each is plotted as a function of wavelength, the dot product of any pulse with any other is zero. Any number of these pulses may be transmitted over the optical medium, for example fiber optic cable, to a series of optical filters. Thus, one or more optical transmission line is the light source for the optical filters. Each optical filter pair in the series may be configured as described above so that it performs the dot product of the light from the fiber optic cable with a particular one of the orthogonal shapes. Thus, the optical filter series compresses the light data into predefined transmission channel components.

Each orthogonal shape may be normalized and/or unitized so that an optical filter such as described above regarding FIGS. 3 and 9 may be used. If a pulse corresponding to any particular filter pair is not present in the light signal, the output from the detectors corresponding to this filter pair is zero. If a pulse is present, the detectors measure a value dependent upon the magnitude of the pulse in the signal. Since this magnitude may be predetermined, the system may be configured to look for a particular level to identify the presence of a pulse. In this way, a far greater number of pulses may be conveyed and recognized over optical media than is possible in conventional systems.

The limit to the number of orthogonal signals may be determined by the modulation frequency of the channel. For example, a 10 GHz data rate on one channel blurs its spectrum by 10 GHz. If Fourier functions are used, the spacing between crests of the most complex filter will not be closer than 10 GHz. This represents the maximum theoretical data transmission rate—approximately 10 to 100 times greater than conventional WDM systems. The Fourier functions may be constructed from etalons, which have sine wave spectra. An etalon is analogous to a pair of mirrors with a spacer between them. Different spacer thicknesses provide different sine functions. An orthogonal system may use WDM channels by transmitting orthogonal functions inside each WDM channel.

As indicated above, the present invention may be utilized in a variety of environments. For example, the process of reading gel electrophoresis plates in conventional genetics testing is relatively time and labor intensive. Using the present invention, light passed through a photograph of a gel electrophoresis plate may be directed to optical filters which compress the light data into orthogonal components corresponding to particular taggants.

Negative Dispersion Filter to Counteract Dispersion in Optical Fibers

Optical filters may affect the phase of light passing through them, and may do so differently at different wavelengths. That is, due to the configuration of the materials comprising the filter, the filter may pass light at different wavelengths at different speeds. Accordingly, the filter creates a phase shift that varies with wavelength over the wavelength range of the incident light. While phase shift is of little or no concern in certain embodiments of the present invention, optical filters may be used in other environments to counteract wavelength dependent phase shift effects present in optical systems.

Fiber optic communications systems provide one such environment. A signal in any medium travels more slowly than the speed of light. As should be understood in this art, a light signal's speed in an optical fiber depends on the material's refractive index. An optical fiber's refractive index, however, varies with the light signal's wavelength, causing the fiber to disperse the signal. That is, because the light signal travels at different speeds at different wavelengths, there is a relative phase shift over the signal's frequency range.

Figure 10A:
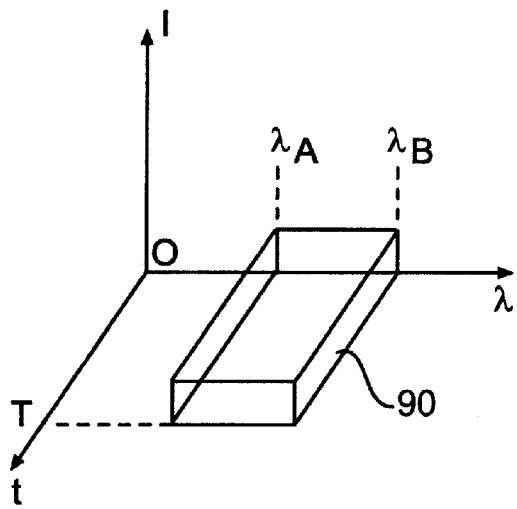
FIG. 10A is a graphical representation of a light pulse.

Referring to FIG. 10A, a light signal pulse 90 is defined by three coordinates I, $\lambda$ and t representing light intensity, wavelength and time, respectively. As shown in the figure, the square-shaped light signal 90 is pulsed on for a time T on a channel that extends at least from $\lambda_A$ to $\lambda_B$.

Figure 10B:
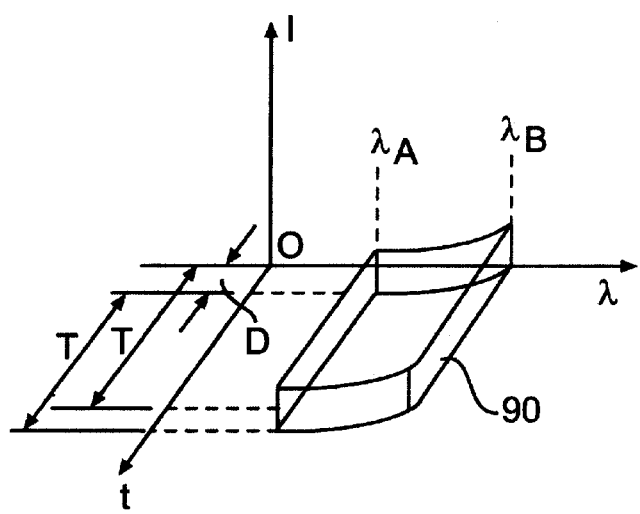
FIG. 10B is a graphical representation of the pulse of FIG. 10A following optical fiber dispersion.

Because the signal travels down a fiber at different speeds over its wavelength range $\lambda_A$–$\lambda_B$, the fiber disperses the signal, for example as shown in FIG. 10B, by the time the signal reaches the fiber's end. As shown in FIG. 10B, light at wavelength $\lambda_B$ traveled at the fastest speed, while light at wavelength $\lambda_A$ traveled at the slowest. Light at intermediate wavelengths traveled at speeds between these extremes, resulting in the dispersed signal shown of FIG. 10B. The shapes of the signals in FIGS. 10A and 10B are provided by way of example only and do not represent actual signals.

The relative phase shift between light at any two wavelengths is predictable. The speeds $S_A$ and $S_B$ of light at wavelengths $\lambda_A$ and $\lambda_B$, for example, may be determined from the fiber's refractive index at each wavelength, as should be understood by those skilled in this art. Assume that speeds $S_A$ and $S_B$ are in units of nm/sec and that the fiber's length is L, in nm. Light at wavelength $\lambda_B$ travels the length of the fiber in $L/S_B$ seconds. In this same time period, light at wavelength $\lambda_A$ travels $S_A(L/S_B)$ nm. The shift D between light at $\lambda_A$ and light at $\lambda_B$ is, therefore, $L-S_A(L/S_B)$, or $L(1-S_A/S_B)$ nm.

Assuming the speed of the slowest traveling light, $\lambda_A$, as a reference, the $\lambda_B$ light's phase shift relative to the $\lambda_A$ light is the number of the signal's wavelengths represented by distance $L(1-S_A/S_B)$. Since the $\lambda_B$ light travels $2\pi$ radians in $\lambda_B$ nm, the $\lambda_B$ light's phase shift relative to the $\lambda_A$ light is $L(1-S_A/S_B)(2\pi/\lambda_B)$ radians.

Signal dispersion may cause interference among sequential signal pulses, particularly where the optical fiber is relatively long. For example, assume that two pulses over the same wavelength range are transmitted over a fiber. If the fastest traveling light in the second pulse overtakes the slowest traveling light in the first pulse, the pulses interfere, and information may be lost.

Optical filters may be constructed to selectively modify phase to prevent such interference. A system may include one or more filters that has a predetermined phase shift at each wavelength to counteract the dispersion caused by the fiber. Given that the phase shift characteristics of a fiber optic cable may be determined as described above, a filter may be designed that substantially or totally reverses the phase shift over the cable to reduce or eliminate phase shift interference. Such a filter may be designed to pass incident light at varying speeds, depending on wavelength, in a manner opposite that of the fiber. Assuming a filter designed to correct dispersion in the fiber described with respect to FIGS. 10A and 10B, for example, light at wavelength $\lambda_A$ is passed through the filter at a first speed, and light at wavelength $\lambda_B$ is passed at a second speed that is slower than the first speed such that the $\lambda_B$ light is again even with the $\lambda_A$ light as it emerges from the filter. The speeds of the light at the wavelengths between $\lambda_A$ and $\lambda_B$ are similarly set so that light at all wavelengths leaves the filter even with the $\lambda_A$ light, thereby reproducing the pulse illustrated in FIG. 10A.

Figure 10C:
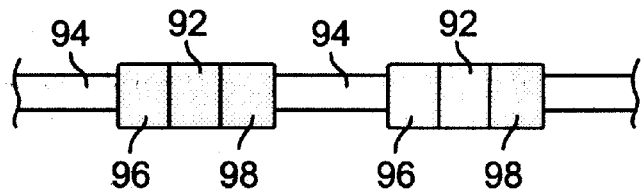
FIG. 10C is a schematic illustration of an optical analysis system according to the present invention.

An optical fiber system may include multiple filters intermittently along a communications line. Referring to FIG. 10C, for example, filters 92 may be disposed between adjacent optical fiber lengths 94 (for example of a length L as described above with respect to FIGS. 10A and 10B). Light from each length 94 is output to a collimating lens 96 that directs the light to its adjacent filter 92. A lens 98 focuses the emerging signal to the next optical fiber length 94.

Optical filters for correcting phase shift may be constructed using techniques similar to one or more of those discussed above, except that a desired phase shift spectrum, not necessarily a desired magnitude transmission spectrum, is the guiding design criteria. An exemplary optical filter design procedure that accounts for phase shift is discussed at J. A. Dobrowolski and D. Lowe, "Optical Thin film Synthesis Program Based on the Use of Fourier Transforms," Applied Optics, Vol.17, No.19, p.3039 (Oct. 1, 1978).

The construction of any particular filter may depend on the length of cable to which it is to be attached. Thus, filters might be constructed for cables of predetermined lengths, for example 1 or 10 kilometers. To correct dispersion in a particular system, as many filters as needed are intermittently installed over the length of cable. For example, if filters are designed for 10 kilometer lengths of a certain type of fiber optic cable, and the system includes a 95 kilometer length of this cable, nine filters may be installed, each at a 10 kilometer interval. Although the remaining 5 kilometers may cause no significant distortion, a filter may be designed for this length as well.

Filter Modifiers and Erbium-Doped Fibers as Superfluorescent Light Source

Erbium doped fibers are sometimes used to amplify signals in fiber optic communications systems. As should be understood in this art, a fluorescing erbium fiber emits radiation in a random pattern. If it is in line with a fiber optic cable, however, it emits two photons along the fiber optic path for each single photon received from the cable. In this manner, the erbium-doped fiber acts as a fiber optic amplifier, the gain of which is typically described in dB. Fibers may be inserted periodically in long fiber optic cables, for example every 10 kilometers, to achieve a desired gain.

Although erbium fibers are traditionally used as amplifiers, they may also be used as light sources in conjunction with optical filter systems as described above. As described in more detail below, erbium fibers may be used to create light signals having a relatively broad, yet limited, wavelength band favorable for the use of Dobrowolski-type optical filters. In addition, optical filters may be produced to modify the light signal from the fibers to a standard predetermined form, thus allowing the use of standard, easily manufactured optical filters.

One problem with conventional fiber optic communication systems is their limited channel bandwidths. Since it is desirable to simultaneously transmit as many signals as possible over each channel, it is desirable in conventional systems to use signals, such as pulses, having as narrow bandwidths as possible. The pulses must be sufficiently separated in wavelength, however, to avoid crosstalk.

As described above, one solution to this problem is to use signals comprising orthogonal pulses which overlap in wavelength. Because the signals can overlap in wavelength, many more signals may be simultaneously transmitted over a single channel than in conventional systems. Because the signals are orthogonal, downstream optical filters are able to compress the data to retrieve the information carried by the signals.

In general, the orthogonal signals are created by passing light through optical filters that output to an optical fiber cable. Each filter's transmission spectrum filters the light to a predetermined spectrum that is orthogonal to the spectra created by the other filters. Pulses are created by pulsing the input light. Because the overlapping signals, which may also be referred to as "channels," are orthogonal, each channel's pulses can be detected by a corresponding downstream filter without interference from the other channels.

There are an infinite number of ways to create a set of orthogonal functions. It may be desirable, however, to standardize these functions to allow the use of standardized filter sets. A set of orthogonal sine waves, for example, can comprise a relatively straightforward set of functions.

The characteristics of light output from these filters, however, depends upon the characteristics of the input light. An optical filter whose transmission pattern defines a sine wave will output a sine wave signal only if the input light has a constant intensity across the filter's wavelength range. If a sine wave output is desired from a non-constant intensity light source, the filter design may be altered to account for the uneven input so that the filter nevertheless produces a sine wave output. In either approach, however, standard, interchangeable filters require a standard light input.

Because the filters' output signal depends on the input light, and because input light differs depending on the light source, an orthogonal filter set for use in systems having different light sources must accommodate the different light input if it is to output a standard set of signals in those systems. In one approach, an orthogonal filter set is created for each different light source. The output spectra of various types of light sources, for example lamps or lasers, are easily measured. Filter sets are created for each source, each filter set being configured to produce orthogonal functions for the particular light pattern produced by its particular light source. Another configuration, however, employs a single filter set that assumes a standard light source spectrum. Modifying filters are made for each light source to modify its output to the standard spectrum. One convenient standard light source output may be a constant intensity ("flat") signal.

The second approach has certain advantages over the first. Primarily, it permits the use of standard filter sets for all optical communications systems. Light sources can be packaged with an appropriate modifying filter or filters so that these light source "packages" can be used interchangeably in any system.

The orthogonal signals of either filter approach discussed above have some operative bandwidth. Because some light sources output light over wider or different bandwidth ranges than others, the choice of a given set of orthogonal functions over a given bandwidth range may preclude the use of light sources which do not output light over that range.

Assuming that the desired standard input light signal is a flat signal, one possible light source is a laser that produces a very sharp, square, narrow bandwidth pulse. This has the advantage of providing flat input light signals to the orthogonal filter set without the use of modifying filters. As indicated above, flat input signals would allow the use of orthogonal filters with sine wave transmission patterns to produce sine wave orthogonal signals. Because the construction of Dobrowolski optical filters depends upon the Fourier transform of the orthogonal transmission functions, construction of sine wave filters is relatively simple. Thus, the use of flat pulses permits the use of easily constructed sine wave filters.

The size of a Dobrowolski filter, however, depends on the signal bandwidth. Because laser pulse bandwidths are so narrow, typically a fraction of a nm, it is generally impractical to create Dobrowolski filters for use with lasers. Even though the use of Fourier components would result in a relatively simple filter design, the filter itself would be very large.

Accordingly, at least when using filters constructed by the Dobrowolski method, it is desirable to use a broad band light to simplify filter construction. A lamp emits light covering hundreds of nm. Lamps are, however, inefficient. They require a relatively great deal of power, and, while they also output a great deal of power, it is distributed over the lamp's entire wavelength range. Thus, there is relatively little output power over the filters' operative bandwidth.

On the other hand, an excited erbium-doped fiber emits light over a relatively broad, yet limited, wavelength range (about 10 nm to 20 nm). Thus, the power output over its output bandwidth is greater than the output over a similar range from a lamp, yet the range is broad enough to permit construction of Dobrowolski filters of an acceptable size.

Figure 11:
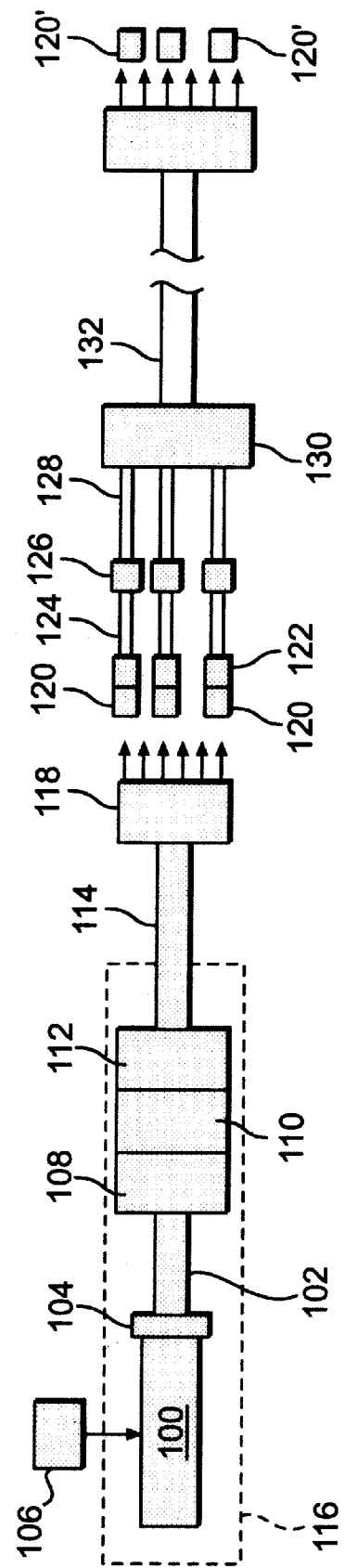
FIG. 11 is a schematic illustration of an optical analysis system according to the present invention.

Referring to FIG. 11, an erbium fiber 100 (or multiple fibers attached end to end) is attached to a fiber optic cable 102 by an optical connector 104. An adjacent laser 106 excites the fiber 100 so that it emits its broader band light into the fiber optic cable. Although the excited erbium fiber emits light in a random pattern, sufficient light is input to the cable to create a suitable signal. The output characteristics of erbium fibers should be understood by those of ordinary skill in the art, and the number of erbium fibers used may be selected according to the requirements of a given system. Furthermore, erbium fiber amplifiers may be used at suitable points to amplify the signal if needed.

The output signal from erbium fiber 100 travels along optical fiber 102 to a collimating lens 108 which directs the light to a modifying filter 110. The modifying filter is, as described above, designed specifically to modify the erbium fiber's output signal to a predetermined output. If a flat signal is desired, for example, the modifying filter may be a Dobrowolski filter having a transmission pattern that passes 100% of the lowest intensity light within the erbium fiber's output spectrum and that scales light at all other frequencies to that level. A lens 112 focuses the flat signal to a fiber optic cable 114 for output to an electrooptic modulation unit. Erbium fiber 100 and modifying filter 110 may be packaged as a unit disposed in a housing 116, that may be interchanged with other light source units.

The electrooptic modulation unit includes a collimating lens 118 that receives and collimates the signal from fiber optic cable 114 and outputs the collimated light to a set of optical filters 120. Each filter 120 filters light received from lens 118 into a light signal that is orthogonal to the signals from every other filter 120. A respective lens 122 focuses the signal from its filter 120 to a fiber optic cable 124 that, in turn, carries its signal to a modulator 126. Each modulator 126 is controlled, for example by a computer or other suitable processing device, to intermittently pass the signal to a respective fiber optic cable 128, thereby creating a series of pulses in such a manner that the number and/or frequency of pulses carries information. If the signal output by unit 116 is a standard shaped signal, the filters 120 may be standard filters generating a set of standard orthogonal functions. A lens 130 receives the orthogonal pulses and focuses them to an output fiber optic cable 132.

A series of downstream optical filters (not shown) receives the signal carried by cable 132. One or more downstream filters filter the same function as a corresponding filter 120 in the electrooptic modulation unit. Thus, the downstream filter(s) detects the presence of each pulse emitted by the modulator 126 of the corresponding upstream filter 120. Since the pulses of the signal on line 132 are orthogonal to each other, each downstream filter detects pulses only from its corresponding upstream filter 120.

Although the upstream filter filters the same function as the downstream filter, the upstream and downstream filters need not be identically constructed. For example, the upstream filter may comprise two physically distinct filters that combine to generate a signal that is detected by a single downstream filter having a transmission spectrum different from that of either upstream filter.

In another embodiment, modifying filters and orthogonal filters are retrofit into existing WDM systems. The WDM systems may transmit a series of individual pulses spaced apart over a particular wavelength range. Orthogonal filter pairs may be inserted into the WDM system to divide the WDM pulses themselves into orthogonal sub-components. This creates a plurality of orthogonal channels within the existing WDM channels.

An exemplary WDM retrofit system could be schematically illustrated by the arrangement shown in FIG. 11 downstream from housing 116. Signals created by a conventional WDM source travel along cable 114 to a collimating lens 118 that outputs to filters 120. A group of filters 120 is provided for each WDM channel, and a filter within each group corresponds to each orthogonal signal. Thus, assuming that there are four WDM channels and that there are four orthogonal signals within each channel, sixteen filters 120 are used.

A bandpass filter may be placed upstream from each filter or filter group to limit the light received by each filter to its corresponding WDM channel. The four filters in each group receive light pulses only within their channel's wavelength range, and each filters this light into a signal that is orthogonal to the signals from every other filter in its group. Although not necessary, the same group of four transmission spectra may be used in each of the other three filter groups. A lens 122 downstream from each filter 120 focuses the filter's output signal to a fiber optic cable 124 that, in turn, carries its signal to a modulator 126. While separate modulators are illustrated in FIG. 11, it should be understood that a single modulator may be used for all filters associated with a single WDM channel. Each modulator may be configured to pulse the orthogonal signals within the period of the WDM pulse to code further information within each pulse.

Again, a series of downstream filters 120' receives the signal carried by cable 132. One or more downstream 120' filters filter the same function over the same wavelength range as a corresponding filter 120. Thus, the downstream filter(s) detects the presence of each pulse emitted by the modulators 126. The downstream filters output to the WDM detection system, which is now able to effectively detect sixteen orthogonal channels over four WDM channels.

Because the WDM pulses are not exactly squared, it may be desirable to include a modifying filter as described above to square each individual WDM pulse. A plurality of standard orthogonal filters, for example using sine functions, can create orthogonal channels within each WDM channel, which can then be transmitted over a single optical line.

Data Metrics

Optical filters may also be employed to detect data reliability problems. In general, an input light spectrum is unreliable when it is significantly different from spectra the system normally processes. In regression vector analysis, for example, samples analyzed by the system should be representative of the samples from which the regression vector was made. If they are not, conclusions drawn from the illuminated samples' light spectrum may be unreliable.

Reliability monitoring methods typically measure some form of distance, for example Euclidian distance, normalized Euclidean distance, or Mahalanobis distance, between one or more sample spectra and a representative spectrum. To determine Euclidean distance, an average spectrum is determined from a number of sample spectra known to be reliable. The distance between a measured spectrum and the resulting average spectrum is the square root of the squared difference between the average spectrum and the measured spectrum at each wavelength.

One way to detect errors in optical filter systems as described herein is to output the intensity of the sample spectrum to a computer which performs a suitable mathematical analysis. It is also possible, however, to estimate these calculations in a manner that can be effected by an optical filter.

Assuming Euclidean distance, for example, between a sample spectrum and an average spectrum over three wavelengths x, y and z, the distance R is described by the following equation:

$$R=((x_A-x_S)^2+(y_A-y_S)^2+(z_A-z_S)^2)^{1/2}$$

where $x_A$, $y_A$, $z_A$ is the intensity of the average spectrum at wavelengths x, y and z and where $x_S$, $y_S$, $z_S$ is the intensity of the sample spectrum at the same wavelengths. The Euclidean distance R varies inversely to the reliability of the sample spectrum. That is, the greater the R value, the greater the distance between the sample spectrum and the average spectrum and the lesser the reliability of the sample spectrum.

Expanding the distance equation, $$R^2=x_A^2-2x_Ax_S+x_S^2+y_A^2-2y_Ay_S+y_S^2+z_A^2-2z_Az_S+z_S^2,$$

or $$R^2=(x_A^2+y_A^2+z_A^2)+(x_S^2+y_S^2+z_S^2)-2(x_Ax_S+y_Ay_S+z_Az_S).$$

If the sample spectrum is similar to the average spectrum, the term $x_S^2+y_S^2+z_S^2$ is approximately equal to $x_Ax_S+y_Ay_S+z_Az_S$. Under this assumption, $$R^2=(x_A^2+y_A^2+z_A^2)-(x_Ax_S+y_Ay_S+z_Az_S).$$

The term $(x_Ax_S+y_Ay_S+z_Az_S)$ is the dot product of the sample spectrum with the average spectrum. Because the intensity values $x_A$, $y_A$, and $z_A$ are known, an optical transmission filter may be constructed to transmit this pattern. For example, assuming "values" of $x_A$, $y_A$, and $z_A$ of 2, 3 and 5, respectively, the filter's transmission spectrum could be 40%, 60% and 100% at respective wavelengths x, y and z. If the exact magnitude of the average spectrum is desired, an amplifier can amplify the filter's output by a factor of five. If this "average spectrum" filter receives and filters the sample spectrum light $x_S$, $y_S$, $z_S$, its output is equal to the dot product $x_Ax_S+y_Ay_S+z_Az_S$.

Figure 12:
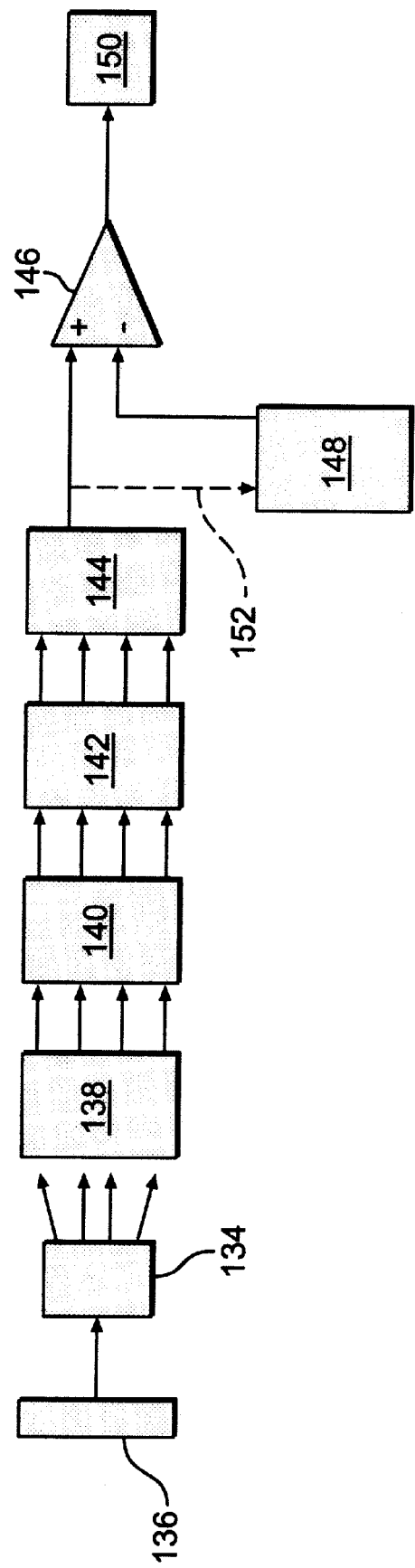
FIG. 12 is a schematic illustration of an optical analysis system according to the present invention.

FIG. 12 schematically illustrates an exemplary arrangement for monitoring sample spectrum reliability by Euclidean distance using the above approximation. A sample 134 is illuminated by a light source 136 so that light from the illuminated sample is received by a collimator 138. A bandpass filter 140 receives the collimated light and passes light within the average spectrum wavelength range to an average spectrum filter 142.

Average spectrum 142 is an optical filter, for example a Dobrowolski type filter, having a transmission spectrum proportional to the average spectrum as explained above. The average spectrum may be determined by measuring the spectra of several samples that are known to be reliable and averaging the values of the spectra at each wavelength. A light detector 144 receives and measures the intensity of the output of filter 142. Light detector 144 may be any suitable light detection device, as should be understood in this art, capable of detecting light intensity over the average spectrum's wavelength range.

Detector 144 outputs an electrical signal to an op amp circuit 146 that compares the signal with a value provided by a sample and hold circuit 148. If the magnitude of the difference between the signals from detector 144 and circuit 148 is more than a predetermined amount, op amp circuit 146 outputs a signal to an output device 150, which may be an LED, a computer, or other suitable downstream processing or display device.

The configuration of a suitable op amp circuit 146 should be understood by those skilled in this art. Similarly, sample and hold circuit 148 can comprise any suitable circuitry, for example including one or more potentiometers, for providing a predetermined voltage level to the op amp circuit. The configuration and construction of these circuits are not essential to the present invention in and of themselves and are therefore not described in detail herein.

The output of sample and hold circuit 148 is preferably a signal equal or proportional to the output of detector 144 when sample 134 is the average sample. To determine this value, a second average spectrum filter (not shown) filters light from a constant intensity light source so that it outputs the average spectrum. For example, assuming the transmission rate of the average spectrum filter is 100% at the wavelength(s) having the highest intensity within the average spectrum and that the transmission rate at each other wavelength is equal to the intensity of the average spectrum at that wavelength as a percentage of the highest intensity, the intensity of light from the constant intensity light source across the filter's operative wavelength range is equal to the highest intensity within the average spectrum. The average spectrum light output from this second average spectrum filter is directed to the average spectrum filter 138 illustrated in FIG. 12. Thus, the output of detector 144 is proportional to or, for example if the detector's output is amplified by an appropriate gain as described above, equal to the dot product of the average spectrum with itself, or $x_A^2+y_A^2+z_A^2$. Sample and hold circuit 148 is automatically or manually set (as indicated at line 152) to this value.

Op amp circuit 14 subtracts the output of sample and hold circuit 148 from the output of detector 144 when filter 142 receives light from a sample 134 as shown in FIG. 12. Since the reliability measure $R^2$ is $(x_A^2+y_A^2+z_A^2)-(x_Ax_S+y_Ay_S+z_Az_S)$, the subtraction of the circuit 148 output, $x_A^2+y_A^2+z_A^2$, from the detector 144 output, is $x_Ax_S+y_Ay_S+z_Az_S$, is equal to $-R^2$.

As discussed above, the output of op amp circuit 14 this signal is equal or proportional (depending on amplification of the filter 142 output in the sample measurements and on the calibration of sample and hold circuit 148) to $-R^2$. Thus, device 150 may be a computing device which logs and/or reports this value and/or which mathematically converts the value to the Euclidean distance R. In other embodiments, an acceptable value of R, and therefore $-R^2$, may be known, and op amp circuit 146 may be configured to output a signal only when the difference between its input signals is beyond that value. In this case, device 150 may be an LED or audible alarm activated by the op amp circuit.

As noted above, the arrangement shown in FIG. 12 operates on the assumption that the sample spectrum is similar to the average spectrum. If an illuminated sample 134 is so different from reliable samples that the assumption does not hold, the output from detector 144 generally differs from the output of sample and hold circuit 148 by a relatively large amount, resulting in an output from op amp 146 indicating unreliable data. That is, the greater the dissimilarity between sample spectra and the average spectrum, the faster that the $-R^2$ value tends to rise, thereby indicating unreliable data.

The same assumption, that the deviation between the sample spectrum and the average spectrum is small, may be used in other distance measurements, such as normalized Euclidean distance and Mahalanobis distance, to remove squared sample spectrum terms, thereby allowing the approximation of the distance measurement through dot product terms effected by optical filters. The Mahalanobis distance is calculated not just using standard deviation normalization, but using the covariance of the wavelengths. If the samples are considered in principal component space rather than as individual wavelengths, the covariance of the space is lost, and it is necessary only to consider the variance of each component at the wavelength of interest. Specifically, $$M=Q-k'B,$$

where M is the Mahalanobis distance, Q is twice the sum of the principal component magnitudes; k' is a proportionality constant, and B is equal to $\Sigma_i x_i b_i$, where $x_i$ is the intensity of the sample spectrum at wavelength i; $b_i$ is $\Sigma_j(l_{ij})/(e_j c_j)$, $l_j$ is the loading of principal component j at the wavelength i; $e_j$ is the relative eigenvalue of principal component j, and $c_j$ is the variance of principal component j. If the data has not been mean centered, the first principal component is the average spectrum. The first term is therefore similar to the term used in the scale-invariant Euclidean metric. This metric is accomplished by calculating the term $\Sigma_j(l_{ij})/(e_j c_j)$ at each wavelength i and preparing an optical filter with transmission scaled to that value. Two filters may be used where the summation yields a negative. Other than this, the process is similar to that discussed above regarding Euclidean distance.

The system illustrated in FIG. 12 may be used within a larger optical filter system. For example, a beam splitter may direct light from sample 138 to a set of optical filters configured to monitor the input signal for one or more characteristics of interest.

Shaping Filters

The use of bandpass filters to assure that only light within the optical filter's operative range is passed to a light detector is discussed above. In a specific embodiment, however, each optical filter in the system is disposed on a substrate which includes the bandpass filter. This permits mass production of bandpass blanks upon which optical filters may be deposited.

The bandpass filter may be constructed from layers of inorganic oxides such as niobium oxide or silicon dioxide by an electron-beam evaporation or reactive magnetron sputtering process, as should be understood by those of ordinary skill in this art. The structure may be designed by an iterative needle method as found in commercially-available programs such as TF-CALC (Software Spectra, Inc.).

The oxide material, and therefore the bandpass filter, may be disposed on a flat, transparent, wafer-like substrate made, for example, of silica. The construction of silica type substrates is commonly understood and is therefore not described herein. The substrate/bandpass filter may then serve as a blank upon which an optical filter, for example a Dobrowolski type filter, is disposed by similar techniques. Dobrowolski filters may be made from oxide type materials in accordance with the Dobrowolski method noted above and may be constructed on the bandpass filter. Since the substrate is transparent, incident light may pass through the substrate and bandpass filter to the optical filter.

Spectrometer on a Chip

Figure 13A:
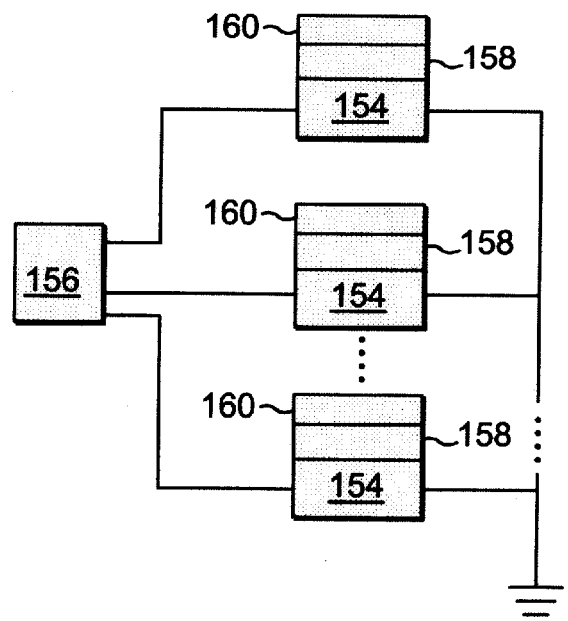
FIG. 13A is a schematic illustration of a photodiode array having optical filters disposed thereon.

In another embodiment of the present invention, optical filters are disposed on photodiode surfaces of a detector array. As should be understood in the art, photodetectors may be constructed from arrays of devices such as photodetectors or photodiodes. Very small (for example approximately 25 micrometers wide) photodiodes may be defined as a semiconductor substrate by a suitable process such as lithographic fabrication so that the resulting chip contains thousands of devices. Referring to FIG. 13A, each photodiode 154 of a photodiode array is comprised of a p-n junction having a certain capacitance that is charged by incident light and is connected by an electrical lead on the chip to an output device 156, for example a data storage and/or processor device such as a computer.

An optical filter 158 having approximately the same dimensions as a photodiode is disposed on each photodiode 154. The optical filters may be Dobrowolski type filters disposed on the photodiodes by a mask or sputtering process. A bandpass filter 160 is disposed on each filter 158 to limit the incident light to the filters operative wavelength range(s).

Each optical filter 154 is constructed to transmit an orthogonal component of the incident light to the photodiode below. Typically, the filters will be used to analyze light about which little is known. Thus, the filters 54 may compress the light data into an appropriate set of orthogonal functions, for example Fourier components. Computer 156 performs the inverse transform of the components to reconstruct the signal. Sets of photodiode/filter pairs, each embodying a set of Fourier functions, may be disposed about the chip.

If the light's principal components are known, each optical filter (or optical filter pair where dual filters are used to account for positive and negative principal component terms) may be a principal component filter. Thus, each photodiode immediately detects the magnitude of the principal component filtered by its optical filter and outputs this magnitude to computer 156 that is in turn programmed to reproduce the incident light from this information. The computer may then perform any desired spectral analysis.

Figure 13B:
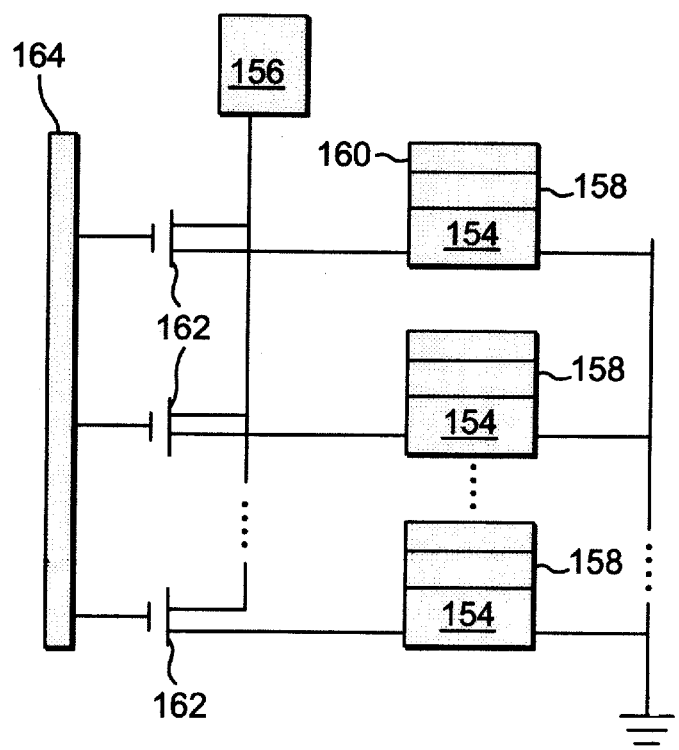
FIG. 13B is a schematic illustration of a photodiode array having optical filters disposed thereon.

FIG. 13A is provided as a functional example of a filter series. Since a very large number of filters will typically be disposed within a detector array, a CCD arrangement as illustrated in FIG. 13B may be appropriate. The output of each filter is connected to a transistor device 162 which is selectively switched open or closed by a shift register 164. The shift register 164 sequentially switches each transistor to output the voltage across the photodiode to computer 156. Computer 156 is programmed to receive the sequential signals, which correspond to identifiable photodiodes 154, and to reconstruct the incident light spectrum or spectra for further analysis.

Accordingly, the optical filters permit the construction of a spectrometer on a small, portable IC chip which can replace conventional spectrometers in existing spectroscopy systems. These IC's enjoy a signal-to-noise advantage over conventional spectrometers, which may lose 70% to typically over 90% of incident light. Losses for the present IC's are generally less than 50%.

ElectroOptic Filters

In another embodiment of the present invention, an optical filter is constructed to have a changeable response. Referring to FIG. 14, optical filter 166 includes an optical filter 168 configured to selectively filter light by wavelength over the filter's wavelength range, for example to effect a regression vector. A filter layer 170 constructed from a non-linear optical material (for example lithium niobate or poled polymer films) or other electrooptic materials such as liquid crystals exhibits refractive indices over the wavelength range of filter 168 that vary in the presence of an electric field. Layer 170 is sandwiched between conductive glass plates 172 and 174. A voltage generated by a voltage/signal source 176, which may include a voltage regulator circuit, applied across layer 170 at plates 172 and 174 changes the refractive indices of layer 170 from a first state to a second state. Since both filters 168 and 170 contribute to the overall transmission spectrum of filter 166, the selective application of voltage 176 across layer 170 changes filter 166 from one transmission spectrum to another.

Both optical filters 168 and 170 may be constructed using the Dobrowolski iterative layering approach. The process begins with a base material having a particular refractive index. Subsequent layers are added in an iterative procedure to achieve a desired transmission spectrum. This is generally done by a computer program. If phase shift is not a concern, there may be many, if not an infinite number of, ways to construct the layers to achieve a desired transmission pattern for the filter.

Creating filter 166 is similar to solving simultaneous equations. Because there may be various ways to make each of the filters 168 and 170, they are designed so that they cooperate to produce a first desired transmission spectrum when voltage 176 is applied across filter 170 and to produce a second desired transmission spectrum when the voltage is not applied. In other words, the requirement that filters 168 and 170 must combine to produce different predetermined transmission under different conditions is a limitation in the layering design for each filter. This process should be relatively straightforward, for example, if filter 166 embodies a Fourier function, since changing the filter's overall refractive index merely shifts from one Fourier function to another.

A filter 166 might be designed to effect a certain regression vector with the voltage across filter 170 is disconnected but to effect the negative of the regression vector with the voltage applied. Thus, light from an illuminated sample may be passed through filter 166 with voltage 176 disconnected so that the filter performs the dot product of the incoming light and the regression vector. When voltage 176 is then applied across filter 170, however, filter 166 applies the negative of the regression vector. If measurements of light intensity under these two conditions are subtracted, the result is proportional to the property to which the regression vector corresponds. This is a convenient way to remove any DC component that may otherwise arise from a variety of causes and that may interfere with accurate measurement.

This configuration also allows construction of a single filter to analyze a sample for multiple properties by selectively applying one or more voltages to particular filter layers. For example, the filter may include several non-linear optical material layers 170 to produce a single filter 166 that can apply multiple functions. The number of desired functions increases the complexity of filter design.

For layer 170 to exhibit the desired non-linear electrooptic characteristic, molecular elements of the material comprising the layer must be aligned to facilitate application of the electric field. This may be achieved by a number of methods of producing non-linear optical material wafers, for example poling or brushing a polymer layer, as should be understood by those of ordinary skill in the art.

In another method, however, a polymer layer is deposited on plate 174, for example by a vaporization technique. Light polarized 90° to the desired direction is applied to the polymer layer to remove molecular elements of undesirable polarization. The light quickly excites and burns away those elements aligned with its polarization. Continued application of the light burns away elements increasingly angularly offset from the light's polarization until elements approaching a 90° offset are removed. The light does not excite the elements disposed at the 90° angle, and those elements will remain in tact within the layer. The duration of the light's application to the polymer layer determines the angle at which elements not exactly aligned in the desirable direction are retained.

Color Separation Filters

Color videography or photography systems typically use three color channels: red, green and blue. In this embodiment of the present invention, optical filters may be used in a color system to detect predetermined characteristics of a sample and to output color signals indicative of these characteristics.

In one exemplary embodiment of the present invention illustrated in FIG. 15, a light source 178 illuminates a sample 180. The sample may be illuminated by any suitable method, for example by reflection of ambient sunlight. A video system camera lens 182 within a housing 184 directs light from sample 180 to a bandpass filter 186 configured to pass light within the operative wavelength range of downstream optical filters 190. A beam splitter 192 separates the light into three light beams, each directed to a respective filter 190.

Each filter 190 directs its output to a detector 194, for example a CCD camera, that is associated with a particular color (for instance red, green or blue). The construction of CCDs and their use within video systems should be understood and is, therefore, not described in detail herein. Briefly, however, each CCD 194 may include an array of photodiodes, each corresponding to a pixel in an electronic image. Because there are three CCDs (one for each of the three colors that may be present in any pixel) in the system illustrated in FIG. 15, there are three photodiodes for each pixel. One or more shift registers simultaneously scan the three CCDs to output the voltage stored at the corresponding photodiode on each CCD to a display device 196. Display device 196, for example a video monitor, receives the three signals and displays at the appropriate pixel a color that is a combination of red, green and blue at intensities determined by the respective signal intensities. The system repeatedly scans for each three-photodiode group the CCD's.

The construction and operation of video systems and their components should be well understood. In conventional systems, the filters upstream from the color filters CCDs pass only the light color with which their downstream CCD is associated. Thus, the light incident on the CCD is the portion of the image received by the video lens consisting of that color. Each photodiode is charged to a level indicative of that color in the image at the photodiode's position. By scanning the photodiodes and combining the information from each three-photodiode group, the system is able to display the image at the display device.

In the video system illustrated in FIG. 15, however, each filter 190 is an optical filter, for example a Dobrowolski type filter, that filters a function, for example a regression vector, that is associated with a particular characteristic of the sample. The light output from each filter is therefore proportional to the strength of the characteristic detected in the light of the sample's image rather than the intensity of a color. Accordingly, the output of any CCD photodiode indicates the degree to which the characteristic with which its filter 190 is associated is present at that area of the image. Display device 196 therefore displays the image in a color scheme that depends upon the relative strength of each characteristic identified by the respective filters 190 at each pixel.

For example, assume the device is contained within a small hand-held housing 184, that the sample 180 is the surface of an aircraft, and that there are three primary characteristics of the surface that contribute to its structural weakness. Filters 190 may be designed as described above to effect a regression vector for light reflected from the surface to identify the presence of each characteristic. When the device is passed over the surface so that light is reflected from the surface to lens 182, the surface's image displayed by device 196 is comprised of a combination of red, green and blue at each pixel indicative of the presence of each characteristic at that position in the image. A color scale may be developed to which the display output may be visually or automatically compared to identify those areas of the aircraft surface in which the three characteristics exist in such proportion to indicate a serious weakness.

It should be understood that FIG. 15 is provided for illustrative purposes only and that the device may be constructed in various suitable manners. For example, the components 182, 186, 192, 190, 194 and 196 may be constructed as a unitary or nonunitary device. Beam splitter 190 may be replaced by other suitable components or arrangements and may be omitted, for example where the filters are all disposed to receive light from filter 186. Furthermore, while three filters respectively associated with three colors are provided to illustrate how the present invention may be utilized within a conventional video system any suitable number of filters and colors may be employed. For example, where the optical filters effect regression vectors that include positive and negative components, two CCDs may be provided for each color, one CCD receiving the output of a positive component filter and the other receiving the output of a negative component filter.

Artificial Neural Network Stages

Neural networks include a series of nonlinear steps each having one or more processing elements. Each processing element may include its own memory and processing capacity so that it performs a predetermined operation upon the information it receives. Each processing element receives one or more inputs and produces a single output which may be directed to as many downstream processing elements as desired. Processing element output signals are transmitted over unidirectional signal channels.

Figure 16:
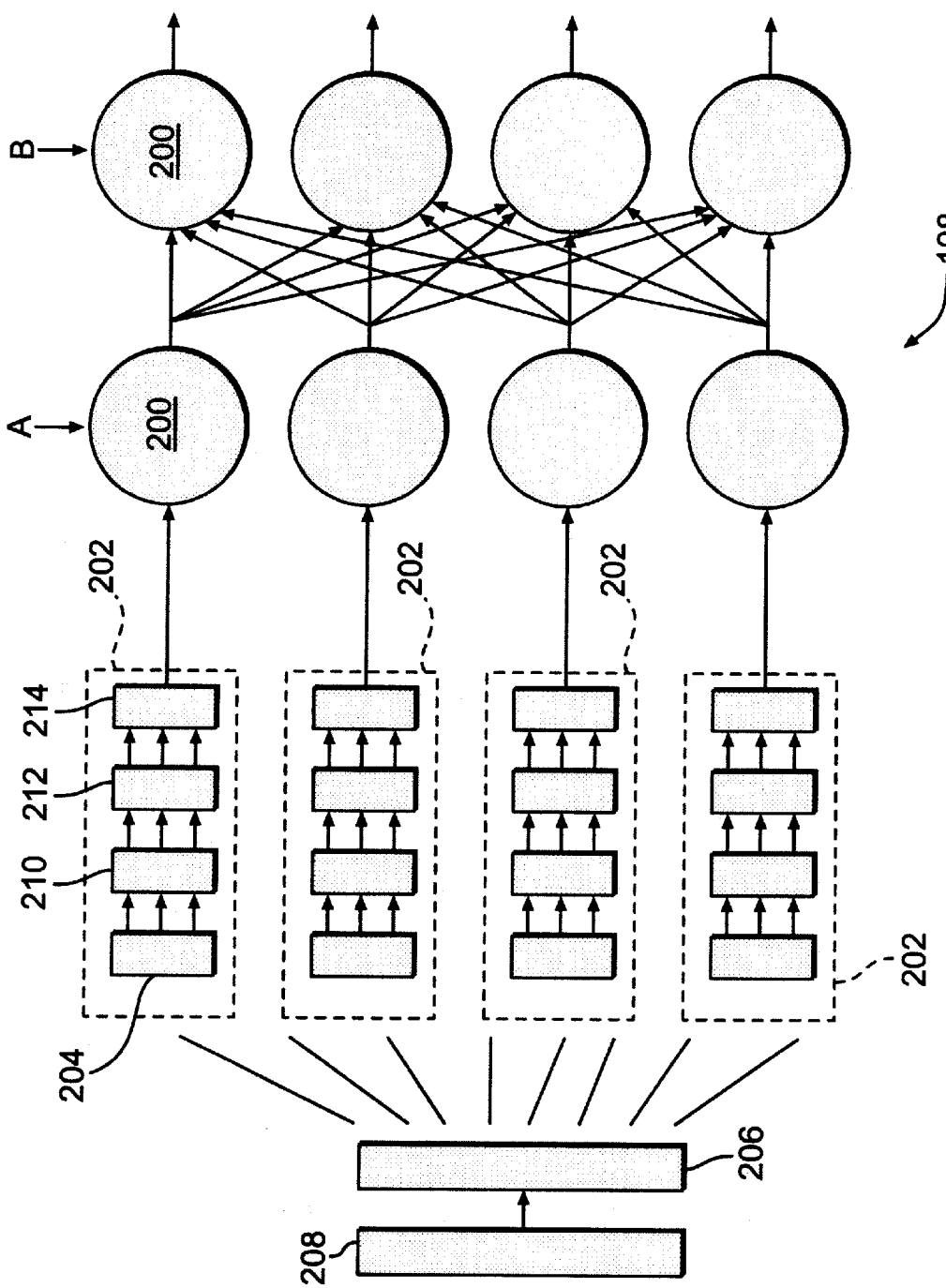
FIG. 16 is a schematic illustration of an optical analysis system according to the present invention.

The architecture and component structure of the various neural network types should be well understood and are not discussed in detail herein. In an embodiment of the present invention, however, optical filters are used to modify data that is input to a neural network processing element. Referring to FIG. 16, a neural network 198 includes an array of processing elements 200. Two processing element stages A and B each include four processing elements 200.

The input to each processing element in stage A is an optical filter arrangement 202. Each arrangement 202 includes a collimating lens 204 receiving light from a sample 206 illuminated by a light source 208 and directing the collimated light to a bandpass filter 210. Bandpass filter 210 limits the light to the wavelength range of an optical filter 212. Optical filter 212 filters light from bandpass filter 210 and outputs the filtered light to a detector 214 which outputs a signal to its corresponding processing element 200.

Accordingly, the output of each optical filter 212 is an input for a processing element 200. Each optical filter may be, for example, a Dobrowolski type filter configured to effect a desired function related to one or more characteristics of the sample 206 that are to be analyzed by network 198. In FIG. 16, for example, each optical filter 212 may effect a regression vector to identify the presence or degree of a certain characteristic of sample 206 through the light from the sample or may embody a principal component or other desired function. This information then becomes data for the network's stage A. It should be understood that the optical filter arrangements are illustrated diagrammatically and that for ease of explanation only a single optical filter 212 is included with each arrangement. It should be understood, however, that more are possible. For example, where a regression vector includes positive and negative component, a dual optical filter arrangement may be employed as discussed above with respect to FIG. 3B.

Hybrid Chemical-Orthogonal Methods

Substances are sometimes contaminated with other substances that are not readily apparent to visual, chemical or spectroscopic analysis. By addition of a certain reagent, however, a new compound is formed that has a larger spectroscopic signature and that is, therefore, more easily detected. For example, the chemical TCE (trichloroethylene) is an environmental hazard that may be almost undetectable when present in water. In the Fujiwara process, for example, a reagent added to TCE-contaminated water reacts with TCE so that the presence of the contaminant is detectable.

Unfortunately, the Fujiwara reagent may react with other substances to produce a very similar color, making visual identification difficult. However, even where the different reactions produce similar colors and spectroscopic signatures, there are differences, and an optical filter according to the present invention may embody a regression vector to identify a particular chemical produced only by the reaction with the searched-for contaminant, thereby eliminating the need for visual inspection and the possible resulting uncertainty. A sample may be analyzed, for example, in a system such as illustrated in FIG. 3A or 3B.

Designer Fluorophores

In DNA systems, fluorescent "tags" may be attached to DNA bases by a DNA sequencer. The DNA is cleared, one base at a time, and the bases are output in a fluid stream through which light is passed to a spectroscope. The resulting spectrum is analyzed to determine which tags are present, thereby identifying the DNA bases.

There are significant limitations with this approach. Primarily, it is relatively imprecise, unless the tags are very different from one another, and tags are therefore typically selected from fluorophores having widely differing spectral signatures. Since each tag must be significantly different from all other tags, the number of available tags is limited. Although the method is sometimes acceptable for DNA, which has only four bases, the limited number of significantly different tags poses a problem regarding proteins, which have twenty-three amino acids.

Figure 17:
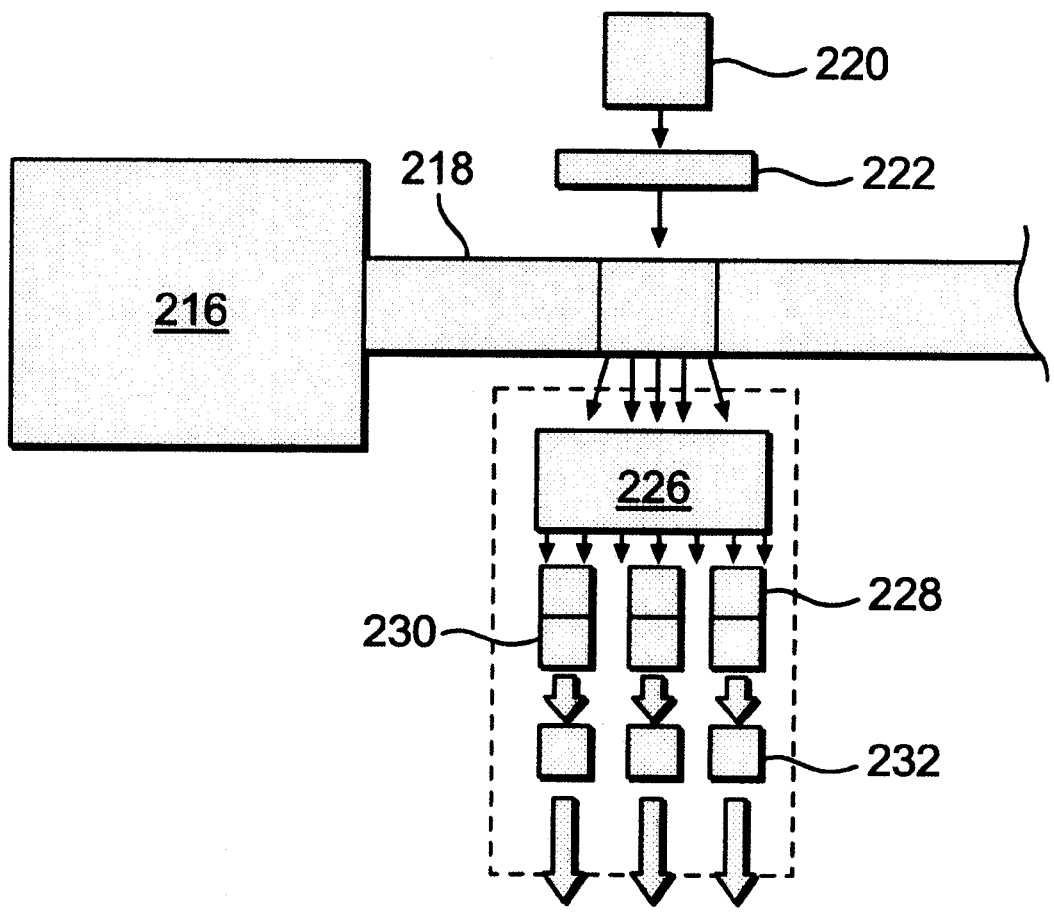
FIG. 17 is a schematic illustration of an optical analysis system according to the present invention.

Optical filters in accordance with the present invention, however, may apply regression vectors to distinguish fluorescent tags, even where the tags are more similar than permissible under conventional methods. For example, referring to FIG. 17, a DNA sequencer 216 applies fluorescent tags to DNA bases and outputs the tagged bases to a fluid stream through a fluid conduit 218. A laser 220 excites the stream through a microscope 222 as it passes through the conduit. Laser 220 may be, for example, an argon or ultraviolet device. A collimator 226 receives the light from the illuminated fluid and directs the light to a series of optical filters 228, each of which effects a regression vector to identify a particular fluorophore tag. It should be understood that a dual filter configuration as discussed above with respect to FIGS. 3A and 3B may be employed where the regression vector includes positive and negative components.

Although three filters are illustrated, it should be understood that any number may be used, depending on the number of fluorophore tags the system employs. Bandpass filters 230 limit the light to the operative wavelength range of the filters 228. Each detector 232 outputs an electrical signal that corresponds to the intensity of the light signal received from a corresponding filter 228 to, for example, a computer. By monitoring the detector outputs, the computer is able to identify specific fluorophore tags.

Autocorrelation Function and Normalization

In one signal normalization method, a signal's magnitude is measured in any suitable and consistent manner (for example at a peak or as integrated over a given wavelength range) to proportionally scale the amplification level of an amplifier. For example, assume a signal is input to an amplifier having a ten times gain that is inversely scaled by the value of a signal input to the amplifier. A detector is placed upstream from the amplifier and is configured to measure the signal's magnitude and to output a corresponding electrical signal to the amplifier, or to a circuit controlling the amplifier, so that the amplifier gain is divided by the signal magnitude. Thus, if the incoming signal has a magnitude of 5, the amplifier gain of 10 is divided by 5 to a gain of 2. If the incoming signal has a magnitude of 10, the amplifier gain is 1. Thus, within the operating range of the amplifier, the magnitude of the amplified signal is always 10.

Figure 18:
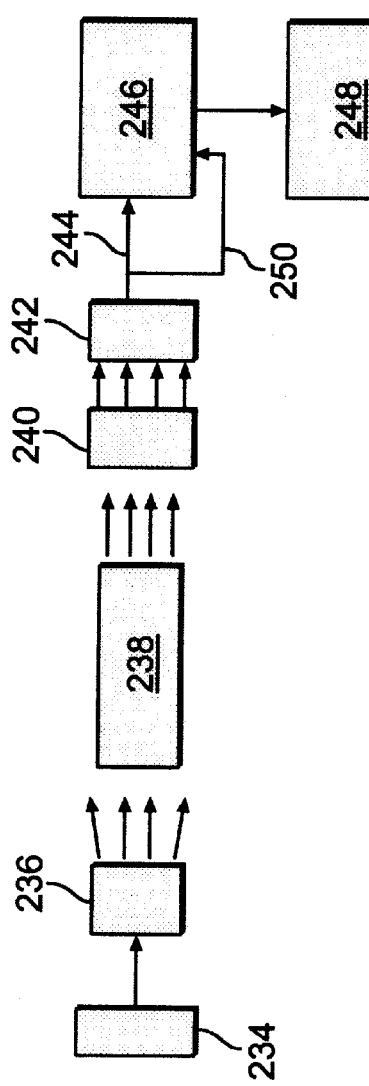
FIG. 18 is a schematic illustration of an optical analysis system according to the present invention.

A system for normalizing an optical filter signal is illustrated in FIG. 18. A light source 234 illuminates a sample 236. A collimator 238 collimates the light and outputs to an optical filter 240, which effects a desired function such as a regression vector. A detector 242 receives the light from the filter and outputs an electrical signal 244 that corresponds to the intensity of the light it detects. Where the regression vector has positive and negative components, a dual filter structure as discussed above with respect to FIGS. 3A and 3B may be used. Signal 244 of FIG. 18 would be output by processor 58 of FIG. 3B.

An amplifier 246 amplifies signal 244, outputting the amplified signal to a computer 248. Amplifier 246 is a variable amplifier having a gain controlled by an input signal 250. Amplifier 246 may be any well understood device, and its particular configuration does not form an essential part of the present invention in and of itself. It may include any associated control circuitry for receiving signal 250 and determining its gain responsively thereto. In this embodiment, the amplifier's gain is understood to be divided by the magnitude of signal 250.

In FIG. 18, signal 250 is equal to signal 244. Thus, amplifier 246 is scaled by the instantaneous magnitude of the signal output by the detector. It should be understood, however, that other scaling factors may be used. For example, an integrating circuit may be disposed along the path of signal 250 so that the amplifier gain is scaled by the average detector output over a predetermined time period. Further, while computer 248 is illustrated as the output device, this is for exemplary purposes only, and the amplifier output may be directed to any suitable downstream processing device, depending on the function of the particular system.

Normalization may be employed to perform an autocorrelation of the input signal, specifically the dot product of the input signal with the input signal average, to indicate the input signal's reliability. The input signal average is predetermined. Where a sufficient number of samples of known reliability are available, the spectrum of each sample may be measured and averaged by wavelength to determine an average spectrum.

If the input signal is equal to the average signal, the dot product of the two is a known value. As the input signal differs from the average, however, the dot product changes from this known value. The magnitude of the change is a measure of the signal's reliability.

In spectroscopy systems, the overall intensity of the input signal generally depends upon the intensity of the light source used to illuminate the sample. Information is carried by the spectral shape of the light from the sample. Since light source intensity tends to vary over time, it is desirable to normalize the input signal in performing the dot product described above. Once the sample signal is normalized, and if the light used to illuminate the samples to determine the average spectrum is of a consistent magnitude or if the average spectra are themselves normalized before determining the sample spectrum, deviation in the dot product is due to differences between the spectral shapes of instantaneous input signals, not to differences in overall signal strength. Accordingly, the dot product is preferably performed between the normalized instantaneous signal and the average spectrum.

In terms of signal vectors, assume that $S_{IN}$ is the normalized instantaneous input light signal, considered as a vector in wavelength space, that $S_I$ is the unnormalized instantaneous input light signal vector, and that $S_A$ is the average input light signal. The dot product of the normalized instantaneous signal and the average signal is:

$$S_{IN} \cdot S_A = (S_I/n.f.) \cdot S_A = (S_I \cdot S_A)/n.f.,$$

where n.f. is a normalization factor.

Figure 19:
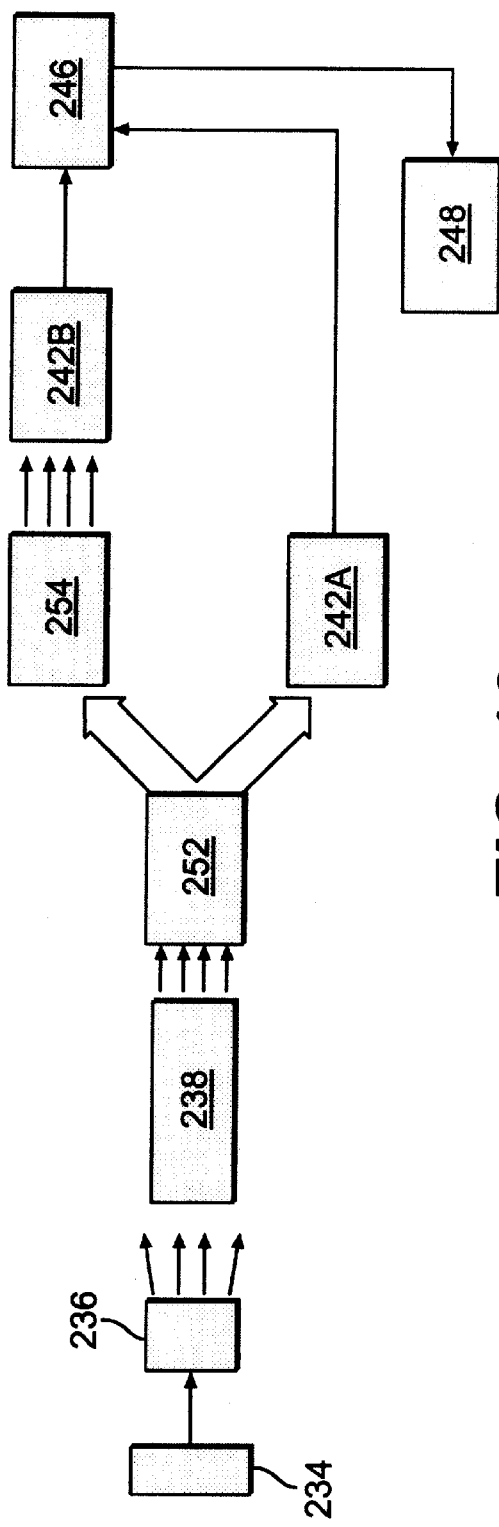
FIG. 19 is a schematic illustration of an optical analysis system according to the present invention.

A system for performing this function, and thereby monitoring signal reliability, is illustrated in FIG. 19. The instantaneous input signal is output from collimator 238 to a beam splitter 252, which directs the signal to an optical filter 254 and to a detector 242A. Although the beam splitter reduces the overall intensity of the two divided signals from that of the input signal, the ratio of the overall intensities of the divided signals is typically unimportant as long as it remains constant, and the output of detector 242A may be suitably used as a normalization factor. Under this condition, the signal output from the beam splitter 252 to filter 254 may be considered $S_I$ in the above equation.

Filter 254 is an optical filter having a variable transmission spectrum patterned after the shape of the average input signal spectrum $S_A$. This pattern is determined by recording and averaging the spectra of several samples as described above. To optimize the signal-to-noise ratio, the transmission rate of filter 254 at the wavelength(s) corresponding to the highest intensity levels in the average spectrum is 100%. The transmission rates at each other wavelength is equal to the ratio of the average-spectrum intensity at that wavelength to the highest average-spectrum intensity.

The output of filter 254 is equal to the dot product of the unnormalized instantaneous input light signal vector and the average input light signal vector, or $(S_I \cdot S_A)$. To divide by the normalization factor, variable amplifier 246, which amplifies the $(S_I \cdot S_A)$ signal received by detector 242B, is scaled by the output of detector 242A. As discussed above, the normalization factor may be configured to any desired form, for example by an integrator circuit.

Computer 248, or other suitable monitoring device, receives the output from amplifier 246 to determine the difference between it and the dot product of the average spectrum with itself. As set forth above, this difference is an indication of input signal quality.

The system illustrated in FIG. 19 may be used within a larger optical filter system. For example, beam splitter 252 may also direct the input signal to a set of optical filters configured to monitor the input signal for one or more characteristics of interest. Thus, computer 248 monitors data quality in real time.

Filter Simplification

Optical filters made by the Dobrowolski method are based on the Fourier transform of the filter function. Accordingly, filter design and construction may be complex where the filter function's Fourier transform contains high-frequency components. Filter design may be simplified, however, if the filter function is separated into segments. An appropriate offset function is added to the segments so that if a filter is constructed for each function segment, subtraction of the segment filters' output is equal to the output of a single filter effecting the original filter function. Segment filter construction may be simplified where the offset function is chosen to minimize the effect of high frequency Fourier components of the segment functions.

Figure 20A:
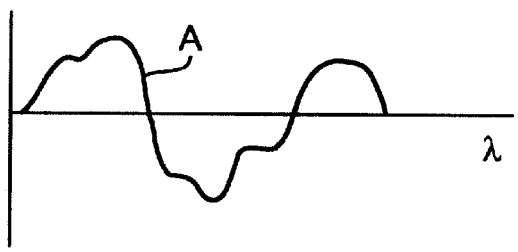
FIG. 20A is a graphical representation of an exemplary transmission spectrum.
Figure 20B:
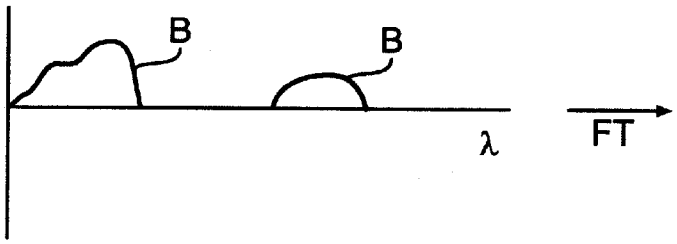
FIG. 20B is a graphical representation of the positive component of the transmission spectrum shown in FIG. 20A.
Figure 20C:
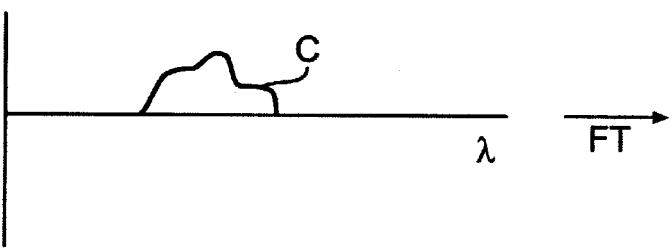
FIG. 20C is a graphical representation of the negative component of the transmission spectrum shown in FIG. 20A.

One convenient manner in which to divide the filter function into segments is by positive and negative values. Referring to FIGS. 20A, 20B and 20C, assume that an exemplary filter function A shown in FIG. 20A is described as a transmission spectrum so that the greatest magnitude point on the graph is positive or negative 100%, depending on whether this point lies on the positive or negative portion. Function A is separated into its positive segment B and its negative segment C in FIGS. 20B and 20C, respectively. Segment C is inversed so that B−C=A. Thus, if optical filters are constructed to embody B and C, their output may be subtracted to achieve the same output as a filter embodying the function A.

If any arbitrary function D (not shown) is added to both B and C, the result is the same. The new functions may be described as B+D and C+D. Their subtraction, (B+D)−(C+D), is still equal to B−C, which is equal to A as described above.

As set forth above, however, functions B and C represent transmission rate patterns with a maximum transmission rate of 100%. There can be no addition to either segment by function D at those wavelengths where the transmission rate is already 100%, and only limited addition where the transmission rate is near 100%. The conflict may be resolved by scaling function A (and therefore functions B and C) so that the maximum transmission rate is less than 100%, by not adding or partially adding function D at those wavelengths where functions B and C are at or near 100%, by defining function D so that it causes no addition to either function over 100% at any wavelength, or by some combination of these approaches. Thus, while the purpose of function D described below is to reduce the complexity of the segment filters, it is also desirable to define and/or implement the function to preserve the integrity of the segment functions.

Figure 20D:
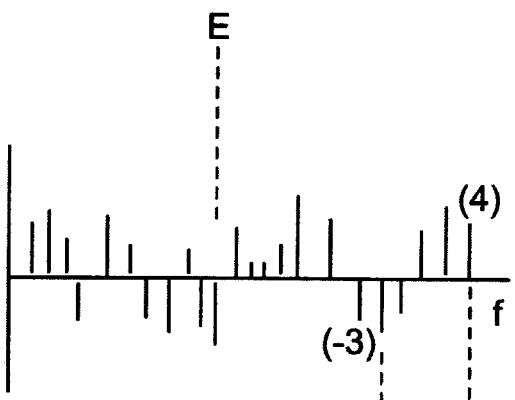
FIG. 20D is a graphical representation of a Fourier transform of the function shown in FIG. 20B.
Figure 20E:
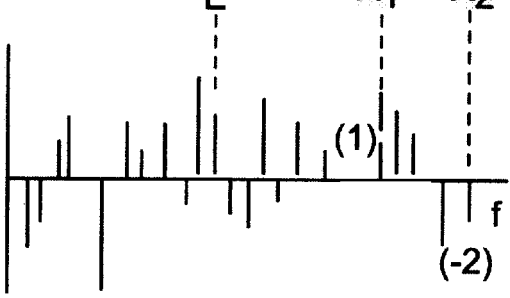
FIG. 20E is a graphical representation of a Fourier transform of the function shown in FIG. 20C.

Function D is defined from analysis of the Fourier transforms of segments B and C, representations of which are provided in FIGS. 20D and 20E, respectively. These graphs are for exemplary purposes only and are not intended to represent the actual Fourier transforms of the functions shown in FIGS. 20B and 20C.

Referring to FIGS. 20D and 20E, a frequency E is chosen above which the two transforms will be minimized. Minimization of the high frequency components reduces filter complexity, and the lower the frequency at which frequency E is selected, the greater the filters are simplified. The magnitude of function D increases, however, as frequency E decreases. Thus, frequency E is chosen to be as low as possible while keeping any effect of function D on data quality as described above within suitable limits. Such limits will depend on the particular circumstances of a given design.

The high frequency Fourier components are minimized by minimizing the "power" of the combined transforms. For example, at frequency $X_1$, the power of the combined transforms is $(-3)^2+1^2=10$. The power at frequency $X_2$ is $4^2+(-2)^2=20$. Obviously, the power at each frequency is minimized if the values of both the 20D and 20E graphs at those frequencies are zero. This is impossible, however, because the same function D must be added to both segment B and segment C. That is, while a value of 3 must be added to bring the B transform to zero at frequency $X_1$, that value would also be added to the C transform at frequency $X_1$, leaving a value of 4 and an overall power of 16. Because the effect of the high frequency transform components is directly related to the combined transform power, this actually increases filter complexity.

Power is minimized, however, where the transform values are averaged at each frequency and where the average is subtracted from both transforms. At frequency $X_1$, for example, the average value is $(-3+1)/2=-1$. When this value is subtracted from both the B transform and the C transform, the transforms have a value of −2 and 2, respectively, resulting in a power of 4. Repeating this process at frequency $X_2$ provides a power of 10.

Accordingly, the Fourier transform of function D at each frequency is determined by averaging the value of the B transform with the value of the C transform at that frequency, for all frequencies above E, and taking the inverse of the result. Inverse transforming this frequency domain function produces the wavelength domain function D. If D is added to both the B and C segments, the resulting segment filters are less complex in design and construction than filters designed from segment functions B and C alone, while providing an equal or approximately equal combined response.

Functions B and C illustrated in FIGS. 20B and 20c are positive at all wavelengths. Function D might have negative components. It is therefore possible that the modified functions B and C might have negative components. This may be accommodated by adding a positive constant value to function D at all wavelengths so that functions B and C are positive at all wavelengths. Because the added constant has no frequency, it adds no complexity to filter construction. It does, however, add to function D's magnitude.

Simplification methods utilizing DC offsets may also be applied to the design of Dobrowolski type filters embodying regression vectors having positive and negative components. Initially, a transmission spectrum is determined from the regression vector so that the entire transmission spectrum is at or between −50% and 50%. The transmission rate at the wavelength(s) having the greatest magnitude may, for example, be set to positive or negative 50%, depending on the sign (positive or negative) of the intensity at each of these wavelengths. The transmission rate at each other wavelength is 50% scaled by the ratio of the intensity at that wavelength (positive or negative) to the magnitude of the greatest intensity. Accordingly, the transmission rate at these wavelengths is between −50% and 50%.

Figure 21:
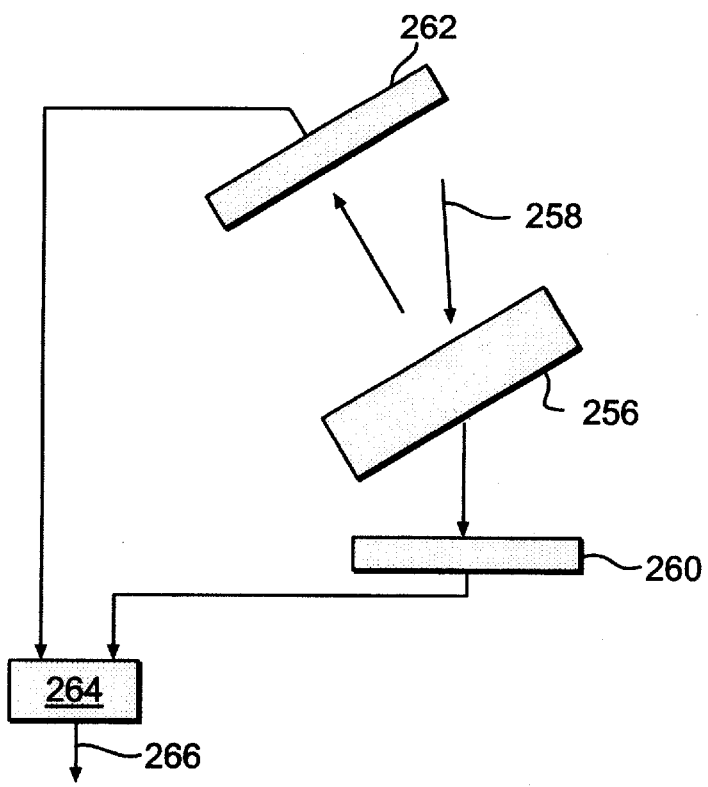
FIG. 21 is a schematic illustration of an optical analysis system according to the present invention.

To determine the filter's transmission spectrum, the regression vector transmission spectrum is increased by 50% at each wavelength. The transmission rates of this "modified" transmission spectrum, therefore, now range from 0 to 100%. Referring to FIG. 21, a Dobrowolski type optical filter 256 effecting the modified spectrum is disposed to operate at a slight angle, for example 10°, with respect to the path of incident light 258 from a sample (not shown). A first light detector 260 is disposed beyond filter 256 to receive the light transmitted thereby. Because filter 256 is not perpendicular to the path of light 258, the filter's transmission spectrum shifts by a certain predictable wavelength distance as described below. This shift is accounted for in the design of filter 256 so that the filter effects the transmission spectrum that is desired if light 256 were normal to filter 256.

Light not transmitted is reflected at an angle of 20° from the path of light 258. Detector 262 is disposed to receive this light. Each of detectors 260 and 262 outputs a signal corresponding to the intensity of its incident light to a processor 264, which may be any suitable device or arrangement (such as a computer or circuitry) capable of performing the appropriate mathematical functions. Processor 264 subtracts the output of detector 262 from the output of detector 260, halves the difference, and outputs a signal equal to this value at 266.

It should be understood that various suitable filter and detector dispositions may be used. For example, rather than designing the filter for operation at a relatively small angle such as 20°, the filter may be designed to operate at a larger angle, such as 45°. Prisms may be used to bring the reflection and transmission side-by-side to a detector pair.

Signal 266 is the signal that would have been output by a light detector receiving light transmitted by an optical filter effecting the original regression vector transmission spectrum had that filter received light 582. Thus, signal 266 is proportional to the dot product of the spectrum of light 258 and the regression vector. To illustrate, assume that R is the original regression vector transmission spectrum (extending from −50% to 50%), that MR is the modified transmission spectrum (offset by 50% and thereby extending from 0 to 100%), and that o is the offset spectrum (positive 50% at each wavelength). Thus, $MR = R + o$, or $MR = R + 50\%$.

If RF is a transmission spectrum describing light reflected from filter 256, $RF = 100\% \text{(at each wavelength)} - MR$, or $RF = 100\% - R - 50\%$, or $RF = 50\% - R$.

The output 266 of processor 264 is, therefore, $\frac{1}{2}(MR - RF) = \frac{1}{2}(R + 50\% - 50\% + R) = R$.

A single filter arrangement as in FIG. 21 may be used in place of the dual filter arrangement as illustrated in FIG. 3B. Further, it should be understood that either a single or a dual filter arrangement, as desired, may be used to effect a vector having positive and negative components as appropriate. Thus, while a single filter associated with a single light detector may be illustrated in various embodiments herein for ease of illustration, it should be understood that either arrangement may be used where needed to accommodate transmission spectra having positive and negative components.

Temperature Correction for Optical Devices

Certain optical filters in accordance with the present invention may be constructed by layers of interference films. Materials, for example certain plastics and transparent oxides, used to make these films have a nonnegligible coefficient of thermal expansion. Specifically, the refractive indices and linear dimensions of the materials may change with temperature change. This may cause the filter's transmission spectrum to shift to longer or shorter wavelengths. Generally, wavelength shifts upward as temperature increases. For example, a certain filter may be designed to have a 70% transmission rate at 900 nm. A given temperature change, however, may cause a wavelength shift so that the 70% transmission rate shifts to 895 nm, with all other transmission rates experiencing a similar shift.

To counter this effect, the filter may be rotated about an axis perpendicular to the light's direction of travel, thereby changing the angle at which the light hits the filter surface. This also causes a wavelength shift, either to longer or shorter wavelengths. The rotation is correlated with the temperature change so that the wavelength shift caused by one counteracts the wavelength shift caused by the other, leaving the filter's resulting transmission spectrum substantially constant.

Once the wavelength shift caused by the filter's thermal expansion is known, the angle of rotation θ needed to counteract the shift can be determined by the following equation:

$\lambda_\theta = (\lambda_0/n)(n^2 - \sin^2\theta)^{1/2}$, where $\lambda_0$ is the wavelength at which a given transmission rate appears before expansion, $\lambda_\theta$ is the wavelength to which this transmission rate shifts due to the expansion, and n is the effective refractive index of the filter materials. Since the filter is comprised of materials having different refractive indices, the effective index of the coating stack is used.

Figure 22:
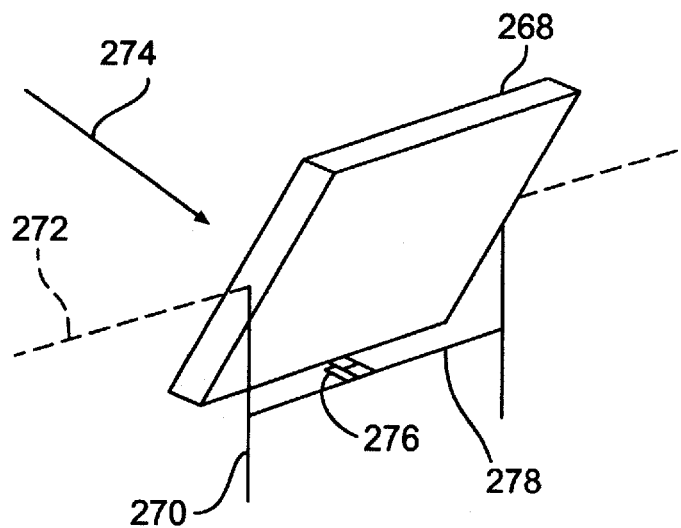
FIG. 22 is a partial perspective view of an embodiment of an optical analysis system according to the present invention.

In one preferred embodiment illustrated in FIG. 22, an optical filter 268 is mounted on a stage, for example a frame 270, so that it is rotatable about an axis 272 perpendicular to the incident light 274. A temperature-sensitive member 276 made of a material that expands and contracts with temperature is attached at one end to the filter and at the other end to a support 278 of frame 270. The expansion and contraction of the element with temperature change rotates the filter on the frame about the axis. The material and dimensions of the element, and its place of attachment to the filter relative to the axis, determine how much the element rotates the filter about the axis. These parameters may be determined by trial and error with a given filter construction or may be predicted if the thermal expansion characteristics of the filter material and of the temperature sensitive material are known.

Spectrum-corrected Light Source

In spectroscopy systems, the spectrum of light from sources such as lamps typically varies with the source's age. When the lamp is new, light from all parts of its filament is similar, resulting in a relatively uniform spectrum. Filaments, however, tend to develop thin spots. Under a constant voltage, current through the filament decreases due to the thin spots' higher electrical resistance. The reduced current causes the non-affected parts of the filament to cool slightly, thereby causing the light from these parts to shift slightly red. The thin spots, on the other hand, become hotter, resulting in a slight blue shift for this light. Thus, the overall spectrum experiences a modest bulge at either end, the majority of the bulge occurring toward the blue. Because information is carried by the spectral shape of light from an illuminated sample, such a change in the light source's spectrum may affect a spectroscopy system's accuracy. The degree to which this is a problem depends on the system's sensitivity and the application for which it is used.

Rather than addressing the change in spectral shape, conventional systems generally focus on output power, which typically decreases in a worn filament as current decreases. To maintain an average light intensity, such systems may employ one or more light or heat detectors proximate the lamp and adjust the filament voltage responsively to the detector. The output of the detector may be directed to a control mechanism that controls the voltage applied to the filament so that as intensity decreases with the development of thin spots, the voltage is increased to offset the power output loss. By addressing only light intensity, these systems fail to account for spectral shape changes that may impact data integrity.

Figure 23:
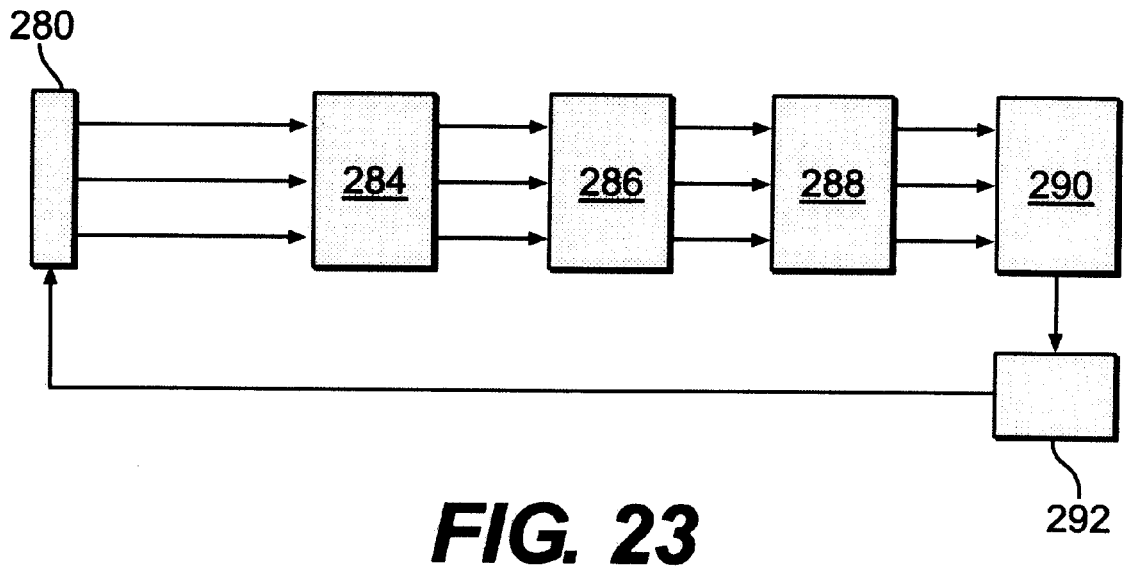
FIG. 23 is a schematic illustration of an optical analysis system according to the present invention.

In contrast, the present invention addresses spectral change. Referring to FIG. 23, a collimator 284 directs light from a light source 280 to a bandpass filter 286 that limits the light to the wavelength range of an optical filter 288. Optical filter 288 has a transmission spectrum effecting a regression vector that identifies change in the spectrum of light source 280. The regression vector may be based on wavelength bands, principal components or other orthogonal components, as described above regarding regression vector analysis. To determine the vector, spectra are measured from several new lamps at the voltage at which they are intended to operate, and these measurements are averaged. Voltage is then varied about the intended voltage (for example +/− 1 or 2 volts). The regression vector is determined by calculating the distance between spectra within this range and the average spectrum and determining the component coefficients as described above. In another method, sample spectra taken from several lamps over an extended period as the lamps age are compared with the average lamp spectrum.

A detector 290 outputs the intensity of the transmitted light to a processor 292 that determines from this information whether the light source spectrum is approximately what it is expected to be. That is, it determines whether or not the output of optical filter 288 is sufficiently close to the output that would be expected if lamp 280 were to emit the average spectrum. If not, the processor adjusts the power input to light source 280 until the detector 290 output indicates that the spectrum is again acceptable.

If the regression vector includes negative components, it may comprise a dual filter arrangement as discussed above with respect to FIG. 3B or a reflection detector arrangement as discussed with respect to FIG. 22. Since light from light source 280 may be employed in a spectroscopy system to analyze a sample, light may be directed to both the sample and to collimator 284 by a beam splitter or other suitable arrangement. Thus, the feedback arrangement illustrated in FIG. 23 may approximately maintain the light source spectrum to maintain the integrity of the analysis performed by that equipment.

Gratings

Figure 24A:
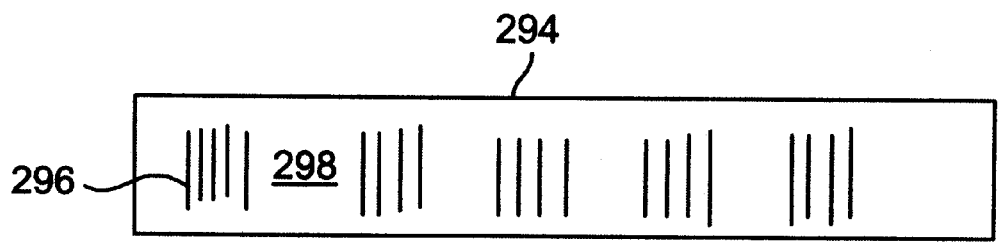
FIG. 24A is a top diagrammatic view of an optical grating.

Optical filters may also comprise gratings designed to compress an incident light signal into a desired function. Optical gratings may be constructed in various well-understood manners. For example, a top view of a volume holographic grating 294 is provided in FIG. 24A. The grating comprises a polymer or gelatin layer whose density varies in a predetermined pattern from higher density regions 296 to lower density regions 298. The density modulation determines the angle at which light at a given frequency is reflected from the grating's surface. Since the reflection angle varies with frequency, reflected light is separated into its spectrum.

Figure 24B:
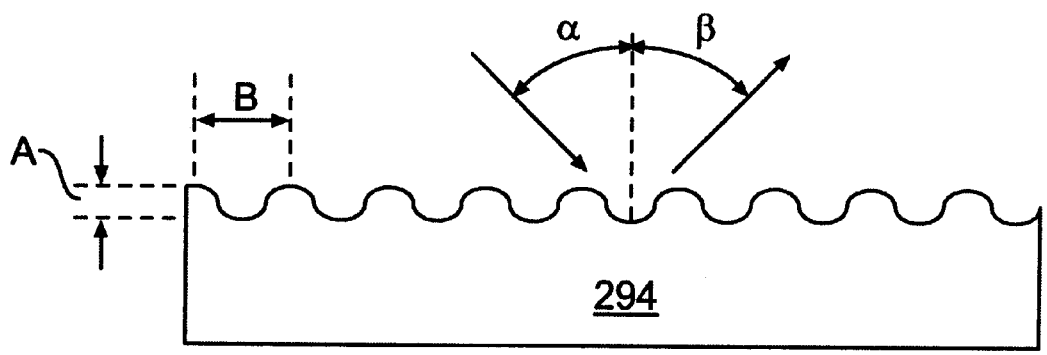
FIG. 24B is a side diagrammatic view of an optical grating.
Figure 24C:
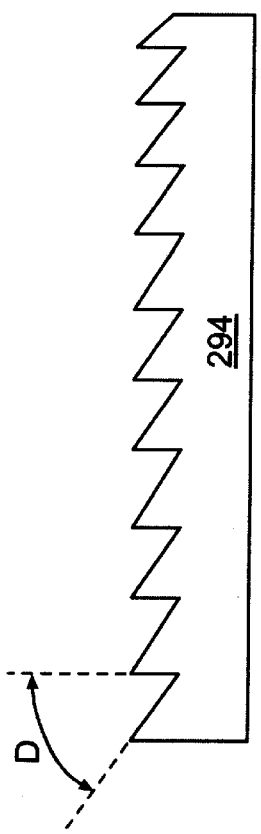
FIG. 24C is a side diagrammatic view of an optical grating.

FIGS. 24B and 24C illustrate side views of two types of grooved reflection gratings, which may be constructed of various suitable materials including metals and polymers. The grooves in the grating 294 of FIG. 24B define a substantially sinusoidal shape and can be formed from a conventional photographic process. The distance A between the grooves' peaks and valleys is the modulation depth, typically less than or equal to 3 or 4 micrometers. The distance B between groove peaks may be used to calculate the groove density (modulation density) C, which is typically within the range of 300 grooves/mm to 4800 grooves/mm. The light's angle of incidence and angle of reflection are indicated at $\alpha$ and $\beta$, respectively.

If the angle of incidence is constant, the angle of reflection depends upon the modulation density C. The intensity of the reflected light depends upon modulation depth A. Referring to density in terms of distance B, $\lambda/B = \sin \alpha = \sin \beta$, where $\lambda$ is the wavelength of the incident light. Thus, assuming that the incident light is polarized (i.e. that $\alpha$ is constant) and that the grating has a uniform density (i.e., that B is constant), the angle of reflection $\beta$ varies with wavelength $\lambda$, and the reflected light is separated into its spectrum.

The grooves of the grating 294 of FIG. 24C define a sawtooth shape which may be formed by a mechanical or laser cutting tool. In this grating, modulation density again affects the reflection angle, but the pitch (or "blaze angle") D is also a factor. If the groove pattern is uniform over the groove, the angle of reflection of polarized light again varies with wavelength, and the grating separates the reflected light into its spectrum.

When a reflection grating is used to separate light into its spectrum, the reflected light is typically directed to a light detector that detects light intensity regardless of the angle at which the light hits the detector. Thus, if a beam of polarized light is directed to a grating and reflected to such a detector, the light intensity at each wavelength can be measured by measuring the intensity of light at the area of the detector corresponding to that wavelength.

Figure 24D:
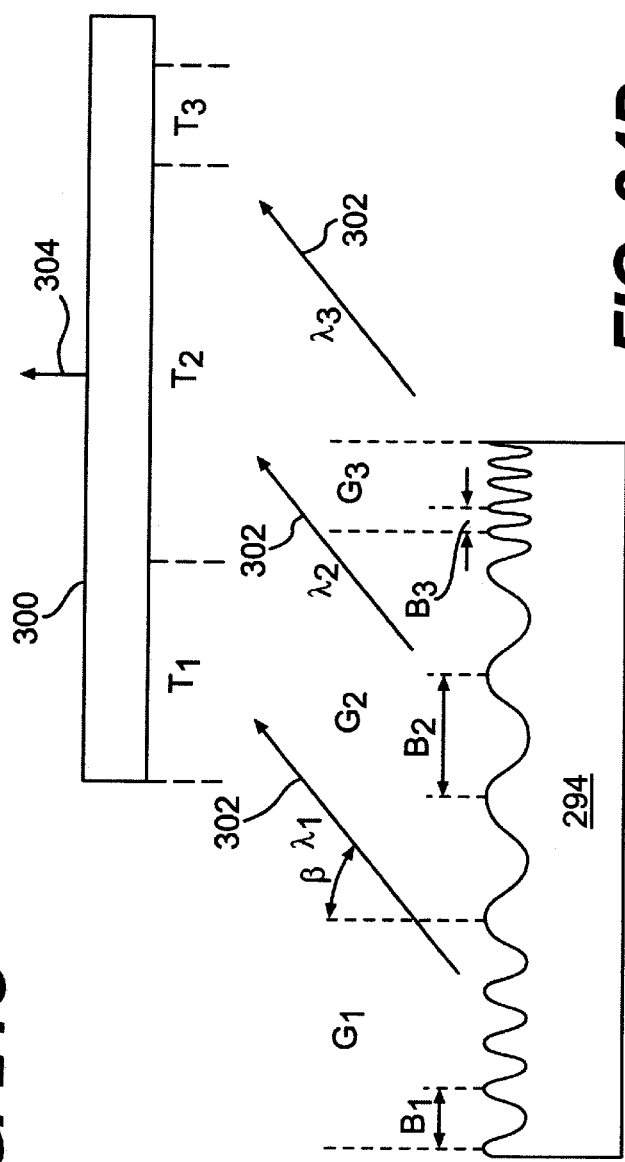
FIG. 24D is a schematic illustration of an embodiment of an optical analysis system according to the present invention and including a side diagrammatic view of an embodiment of a grating-type optical filter.

Referring to FIG. 24D, however, a target light detector 300 detects light at only one angle of incidence. The detector detects no incoming light at other angles. A grating 294 includes three regions $G_1$, $G_2$ and $G_3$ having grooves separated by different modulation distances $B_1$, $B_2$ and $B_3$, respectively. Detector 300 is disposed with respect to grating 294 so that light 302 reflected from grating 294 at an angle β is received by detector 300 at its operative angle of incidence. Thus, the detector measures the intensity of light 302. Detector 300 may be constructed from a lens or mirror that focuses parallel light 302 to a conventional light detector.

Because the modulation density of grating 294 varies among regions $G_1$, $G_2$ and $G_3$, the regions reflect light at angle β having different wavelengths $\lambda_1$, $\lambda_2$ and $\lambda_3$, respectively. Accordingly, if polarized light is directed to the entire surface of grating 294, target area $T_1$ of detector 300 receives only light of wavelength $\lambda_1$, target area $T_2$ receives only light of wavelength $\lambda_2$, and target area $T_3$ receives light only of wavelength $\lambda_3$. A mirror may be disposed between grating 294 and detector 300. Since light 302 has a known angle of incidence to the mirror and, therefore, a known angle of reflectance, the detector may be disposed with respect to the mirror to receive and detect the reflected light 302.

By varying the areas of regions having certain modulation densities, an optical filter 294 as in FIG. 24D may be configured to compress light data as do the Dobrowolski filters described herein. For example, assume a Dobrowolski filter transmits 50% of light of wavelength $\lambda_1$, 100% of light of wavelength $\lambda_2$ and 25% of light at wavelength $\lambda_3$. A grating 294 as in FIG. 24D may effect a function having the same spectral shape where area $G_1$ is half of area $G_2$, and area $G_3$ is one-fourth of area $G_2$. The output 304 of detector 300 is therefore proportional to the dot product of the incident light and the function effected by optical filter 294.

Although modulation density is used as the variable in the embodiment illustrated in FIG. 24D, it should be understood that pitch may also be used.

IR Up-Conversion Materials

Direct detection of infrared light is sometimes difficult when using visible light detectors. There are certain well-known materials that, however, when energized by a laser, receive infrared photons and release photons of visible light. These materials are used in infrared light detectors to receive infrared light. Their visible light output is proportional to the amount of received infrared light and is directed to a visible light detector. Thus, the output of the visible light detector is proportional to the input infrared light.

Figure 25:
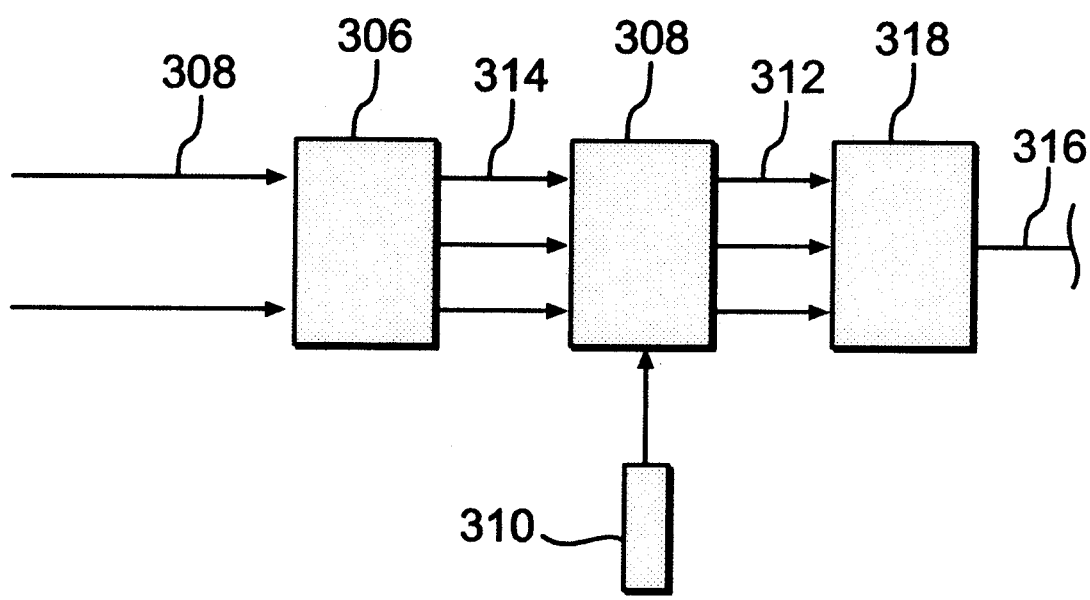
FIG. 25 is a schematic illustration of an optical analysis system according to the present invention.

This combination of devices may be used as a detector in the optical filter systems discussed herein to facilitate the use of these systems for IR chemical imaging. Referring to FIG. 25, an optical filter 306 filters light 308 from a sample (not shown) and outputs the filtered light to an IR conversion unit 308 energized by a laser 310. The intensity of the visible light 312 output by unit 308 is proportional to the infrared light of incident light 314. Accordingly, the output signal 316 of a visible light detector 318 is a measure of the infrared light content of incident light 314.

While preferred embodiments of the invention have been described above, it should be understood that any and all equivalent realizations of the present invention are included within the scope and spirit thereof. Thus, the embodiments depicted are presented by way of example only and are not intended as limitations upon the present invention. Therefore, it is contemplated that any and all such embodiments are included in the present invention as may fall within the scope of the appended claims.

What is claimed is:

1. A neural network system, said system comprising:

an array of processing elements, wherein each said element performs a respective predetermined operation on one or more input signals and outputs a resulting signal to one or more other said elements or to an output device; and an optical filter that weights the intensity of a light signal from an illuminated sample by wavelength according to a regression vector, wherein said regression vector corresponds to the combination of a plurality of weighted orthogonal components of said light signal, wherein each said orthogonal component is weighted according to the amount of data it carries related to the presence of a predetermined physical characteristic in said sample and wherein said orthogonal components comprise a compression of data carried by said light signal, and that outputs a signal corresponding to said weighted light signal to a said element.

2. The system as in claim 1, including a plurality of said optical filters.

3. The system as in claim 1, including a collimating lens disposed between said sample and said optical filter to collimate said light signal and direct said light signal to said optical filter.

4. The system as in claim 3, including a bandpass filter disposed between said collimating lens and said optical filter, said bandpass filter passing a wavelength range of said light signal at least within an operative wavelength range of said optical filter.

5. A neural network system, said system comprising:

an array of processing elements, wherein each said element performs a respective predetermined operation on one or more input signals and outputs a resulting signal to one or more other said elements or to an output device; and a plurality of optical filters, wherein each said optical filter weights the intensity of a light signal from an illuminated sample by wavelength according to a regression vector, wherein said regression vector corresponds to the combination of a plurality of weighted orthogonal components of said light signal, wherein each said orthogonal component is weighted according to the amount of data it carries related to the presence of a predetermined physical characteristic in said sample and wherein said orthogonal components comprise a compression of data carried by the light signal, and outputs a signal corresponding to said weighted light signal to a respective said element.

* * * * *

UNITED STATES PATENT AND TRADEMARK OFFICE
CERTIFICATE OF CORRECTION

| | | |
|---|---|---|
| PATENT NO. | : 6,529,276 B1 | Page 1 of 1 |
| APPLICATION NO. | : 09/286881 | |
| DATED | : March 4, 2003 | |
| INVENTOR(S) | : Michael L. Myrick | |

It is certified that error appears in the above-identified patent and that said Letters Patent is hereby corrected as shown below:

Col. 1, line 2 following the Title of the Invention please add:

--The U.S. Government has a paid-up license in this invention and the right in limited circumstances to require the patent owner to license others on reasonable terms as provided for by the terms of Grant No. N00014-97-1-0806 awarded by the Office of Naval Research and Grant No. F33615-00-2-6059 awarded by the Air Force Research Laboratory.--

Signed and Sealed this

Fifteenth Day of February, 2011

David J. Kappos
*Director of the United States Patent and Trademark Office*